(12) United States Patent
Schwartz et al.

(10) Patent No.: US 6,605,710 B2
(45) Date of Patent: Aug. 12, 2003

(54) GENE WHOSE EXPRESSION PROMOTES DIFFERENTIATION OF MYELOID PROGENITOR CELLS INTO NEUTROPHILS AND/OR MONOCYTES/MACROPHAGES

(75) Inventors: Richard C. Schwartz, Haslett, MI (US); Qiang Tian, Kenmore, WA (US)

(73) Assignee: Board of Trustees of Michigan State University, East Lansing, MI (US)

( * ) Notice: Subject to any disclaimer, the term of this patent is extended or adjusted under 35 U.S.C. 154(b) by 0 days.

(21) Appl. No.: 09/758,623

(22) Filed: Jan. 11, 2001

(65) Prior Publication Data

US 2002/0108137 A1 Aug. 8, 2002

(51) Int. Cl.[7] .................... C07H 21/04; C12N 15/74; C12N 5/02; C12N 15/09; C12P 21/06
(52) U.S. Cl. .................... 536/23.1; 536/23.5; 536/23.4; 435/320.1; 435/325; 435/455; 435/69.1
(58) Field of Search .................... 536/23.1; 435/320.1, 435/69.1, 325, 455

(56) References Cited

PUBLICATIONS

Rudinger Characteristics of the amino acids as components of a peptide hormone sequence pp. 1–7 Jun. 1976.*
Bowie et al. Deciphering the message in protein sequences: tolerance to amino acid substitutions vol. 247 pp. 1306–1310.*
Scott et al., Blood 80:1725–1735 (1992).
Natsuka et al., Blood 79:460–466 (1992).
Radomska et al., Mol. Cell. Biol. 18:4301–4314 (1998).
Zhang et al., Proc. Natl. Acad. Sci. USA 94:569 (1997).
Liu et al., Immunity 5:491–501 (1996).
Zhang et al., J. Exp. Med. 188:1173–1184 (1998).
Akira et al., Embo J. 9:1897–1906 (1990).
Kinoshita et al., Proc. Natl. Acad. Sci. USA 89:1473–1476 (1992).
Poli et al., Cell 63:643–653 (1990).
Chang et al., Mol. Cell. Biol.10:6642–6653 (1990).
Descombes et al., Genes Dev. 4: 1541–1551 (1990).
Furutani et al., Nuc. Acids Res. 14:3167–3179 (1986).
Lowenstein et al., Proc. Natl. Acad. Sci. USA 90:9730–9734 (1993).
Shirakawa et al., Mol. Cell. Biol. 13:1332–1344 (1993).
Zhang and Rom, Mol. Cell. Biol. 13:3831–3837 (1993).
Bretz et al., Proc. Natl. Acad. Sci. USA 91:7306–7310 (1994).
Hu et al., J. Immunol. 160:2334–2342 (1998).
Williams et al., J. Biol. Chem. 273:13493–13501 (1998).
Chumakov et al., Mol. Cell. Biol. 17:1375–1386 (1997).
Chih et al., Blood 90:2987–2994 (1997).
Morosetti et al., Blood 90:2591–2600 (1997).
Yamanaka et al., Proc. Natl. Acad. Sci. USA 94:6462–6467 (197).
Yamanaka et al., Proc. Natl. Acad. Sci. USA 94:13187–13192 (1997).
Verbeek et al., Blood 93:3327–3337 (1999).
Coutts et al., Blood 93:3369–3378 (1999).
Chen et al., Blood 90:156–164 (1997).
Saisanit and Sun, Mol. Cell. Biol. 17:884–850 (1997).
Iwama et al., Nuc. Acids Res. 26:3034–3043 (1998).
Valteri et al., J. Immunol. 138:3829–3835 (1987).
Tsai et al., Genes & Dev. 8:2831–2841 (1994).
Tasi and Collins, Proc. Natl. Acad. Sci. USA 90:7153–7157 (1993).
Pear et al., Proc. Natl. Acad. Sci. USA 90:8392–8396 (1993).
Donner et al., J. Virol. 41: 489–500 (1982).
Peters et al., Eur. J. Biochem. 182: 507–516 (1989).
Fort et al., Nuc. Acids Res. 13:1431–1442 (1985).
Morgenstern and Land, Nuc. Acids Res. 18:3587–3596 (1990).
Sompayrac and Danna, Virol. 200:849–853 (1994).
Williams, et al., Genes & Dev. 5: 1553–1567 (1991).
Mann et al., Cell 33: 153–159 (1983).

* cited by examiner

*Primary Examiner*—Anne M. Wehbe'
*Assistant Examiner*—Qian J Li
(74) *Attorney, Agent, or Firm*—Ian C. McLeod

(57) ABSTRACT

The present invention provides a human gene sequence that encodes the CDDP-1 polypeptide, which is involved in cell differentiation, in particular differentiation of undifferentiated progenitor cells into neutrophils, monocytes/macrophages, mast cells, and/or erythroid cells. Assays for detecting CDDP-1 expression, vectors that express CDDP-1, methods for using CDDP-1 to induce or promote cell differentiation, and transgenic animals deficient in one or both CDDP-1 alleles are described.

11 Claims, 21 Drawing Sheets

```
            10                    30                    50                          70                        90
GNCCCTCGACGGCNTGCAGCCGGGAGAGCCATGGCGGGGGCCGCAGCGGGCGGCAGAGGCGGAGGTGCCTGGGGGCCGGGGCGCGGAGGG
                                M  A  G  A  A  A  G  G  R  G  G  G  A  W  G  P  G  R  G  G
                        110                    130                   150                    170
GCCGGGGGGCTCCGGCGGGGCTGCTCTCCCCCAGCCCCCGCCGGCTCCCCCGGGCTGGGCTGCAGCCGCTCAGGGCCACGATCCCCTTC
 A  G  G  L  R  R  G  C  S  P  P  A  P  A  G  S  P  R  A  G  L  Q  P  L  R  A  T  I  P  F
         190                    210                   230                    250                   270
CAGCTGCAGCAGCCGCACCAGCGCCGGGACGGGGGTGGCCGTGCAGCCAGCGTCCCATGCTCGGTGGCCCCAGAAAAGTCAGTGTGTAGG
 Q  L  Q  Q  P  H  Q  R  R  D  G  G  R  A  A  S  V  P  C  S  V  A  P  E  K  S  V  C  R
                 290                    310                   330                    350
CCTCAGCCACTTCAGGTCCGGCGTACATTCTCCCTGGACACCATCCTCAGCTCCTACCTTCTGGGCCAGTGGCCACGAGATGCTGATGGG
 P  Q  P  L  Q  V  R  R  T  F  S  L  D  T  I  L  S  S  Y  L  L  G  Q  W  P  R  D  A  D  G
         370                    390                   410                    430                   450
GCCTTCACCTGCTGCACCAATGACAAGGCCACCCAGACGCCCCTGTCCTGGCAAGAGCTAGAAGGTGAGCGTGCCAGTTCCTGTGCACAC
 A  F  T  C  C  T  N  D  K  A  T  Q  T  P  L  S  W  Q  E  L  E  G  E  R  A  S  S  C  A  H
                 470                    490                   510                    530
AAGCGCTCAGCATCCTGGGGCAGCACAGACCACCGAAAAGAGATTTCCAAGTTGAAGCAACAACTGCAGAGGACGAAGCTGAGCCGCAGT
 K  R  S  A  S  W  G  S  T  D  H  R  K  E  I  S  K  L  Q  Q  L  Q  R  T  K  L  S  R  S
         550                    570                   590                    610                   630
GGGAAAGAGAAGGAGCGAGGTTCACCACTCCTAGGGGACCACGCAGTGCGGGGAGCACTGAGGGCGTCCCCTCCCAGCTTCCCCTCAGGG
 G  K  E  K  R  G  S  P  L  L  G  D  H  A  V  R  G  A  L  R  A  S  P  P  S  F  P  S  G
                 650                    670                   690                    710
TCCCCTGTCTTGCGACTCAGCCCCTGCCTGCACAGGAGCCTGGAAGGGCTCAACCAAGAGCTGGAGGAGGTATTTGTGAAGGAGCAGGGA
 S  P  V  L  R  L  S  P  C  L  H  R  S  L  E  G  L  N  Q  E  L  E  E  V  F  V  K  E  Q  G
         730                    750                   770                    790                   810
GAAGAGGAGCTGCTGAGGATCCTTGATATCCCTGATGGGCACCGGGCCCCAGCTCCTCCCCAGAGTGGCAGCTGTGATCATCCCCTCCTC
 E  E  E  L  L  R  I  L  D  I  P  D  G  H  R  A  P  A  P  P  Q  S  G  S  C  D  H  P  L  L
                 830                    850                   870                    890
CTCCTGGAGCCTGGCAACCTTGCCAGCTCTCCTTCCATGTCCTTGGCATCTCCCCAGCCTTGTGGCCTGGCCAGTCATGAGGAACATCGG
 L  L  E  P  G  N  L  A  S  S  P  S  M  S  L  A  S  P  Q  P  C  G  L  A  S  H  E  E  H  R
         910                    930                   950                    970                   990
GGTGCCGCCGAGGAGCTGGCATCCACCCCCAACGACAAAGCCTCCTCTCCAGGACACCCAGCCTTTCTTGAAGATGGCAGCCCATCTCCA
 G  A  A  E  E  L  A  S  T  P  N  D  K  A  S  S  P  G  H  P  A  F  L  E  D  G  S  P  S  P
                 1010                   1030                  1050                   1070
GTCCTTGCCTTTGCTGCCTCCCCTCGACCTAATCATAGCTACATCTTCAAACGGGAGCCCCCAGAAGGCTGTGAGAAAGTGCGTGTGTTT
 V  L  A  F  A  A  S  P  R  P  N  H  S  Y  I  F  K  R  E  P  P  E  G  C  E  K  V  R  V  F
         1090                   1110                  1130                   1150                  1170
GAAGAAGCCACGTCTCCAGGTCCTGACCTGGCCTTCCTGACTTCCTGTCCTGACAAGAACAAAGTCCATTTCAACCCGACTGGCTCAGCC
 E  E  A  T  S  P  G  P  D  L  A  F  L  T  S  C  P  D  K  N  K  V  H  F  N  P  T  G  S  A
                 1190                   1210                  1230                   1250
TTCTGCCCCGTCAACCTGATGAAGCCCCTCTTCCCCGGCATGGGCTTCATCTTCCGTAACTGCCCCTCAAACCCGGGATCTCCCCTTCCC
 F  C  P  V  N  L  M  K  P  L  F  P  G  M  G  F  I  F  R  N  C  P  S  N  P  G  S  P  L  P
         1270                   1290                  1310                   1330                  1350
CCGGCCAGCCCCAGGCCACCACCTCGGAAGGATCCGGAAGCCTCCAAGGCCTCCCCACTGCCATTCGAGCCATGGCAGCGCACCCCACCA
 P  A  S  P  R  P  P  R  K  D  P  E  A  S  K  A  S  P  L  P  F  E  P  W  Q  R  T  P  P
                 1370                   1390                  1410                   1430
TCAGAAGAGCCTGTGCTTTTCCAGAGCTCCCTGATGGTCTGAGGGTCCCACCCCTGCCCCACTTTACCATAGAGACCAGTGCCTTGGTGG
 S  E  E  P  V  L  F  Q  S  S  L  M  V  *
         1450                   1470                  1490                   1510                  1530
CAGGTCCCTCCCCAGGTCCCCTGAGATGGGGTATGGAGGGGCCCTTCCCTCTCGGCCTTCGAGCACTTTCTTTCACTTACTGTGTCAAAG
                 1550                   1570                  1590                   1610
CCCTGGGTCCTCTTTTTGATGGGCACCGGCCCCTCTGAACGTGATGGGACCTGCCTTCTCCACTAGTAGCTGGGCAGCTCACAATTCACA
         1630                   1650                  1670                   1690                  1710
CCTGTGTACCTGCCACATCCCTCACTTGGTGGAAAACACCCAGAAGGTCTTGAGTCCCCCACCCCTGGGTGTCAGTCCAAATGACTGTAT
                 1730                   1750                  1770                   1790
AGGAGGCCCTTATTTTTGTCACAGAGCAAGCTGGCCATGAACGAAGGAGAGAAGACGCCACAGATTTCCTTCCCTCTCCTCCAGGAGACC
         1810                   1830                  1850                   1870                  1890
ATAAGATAGATCCCCCATCCTCTCAGCCCTATTCCCATGCCTCCCTCTCATTGGAGGAGCTGACCAAAGCAGCCCTAACGGGCCATAACA
                 1910                   1930                  1950                   1970
CTTGACCAATTCAGCTGCTGGCAGAGGGAGGAAACAAGTGTTTTCCCAAGTGGCATTTTCATCTCGCTTTCACCCTGACTAAAGATTGTC
         1990                   2010                  2030                   2050                  2070
TTAAGTAGCAGCCCAGCCCGCCCAGGTGGGTAGTGGGAGGAGAGCTGGCATTCCTCCAGGTGGCAAATGGCGACTCTATACTC
                 2090                   2110                  2130                   2150
TCCGCCCGCCCCAGGGCTGGATGGATTAGAAAAATCCCTATTTTTCTTGTATCGATGTAGAGACTCTATTTTCTCCCAAAGACACTATTT
         2170                   2190                  2210                   2230                  2250
TTGCAGCTGTTTGAAGTTTGTATATTTTCCGTACTGCAGAGCTTACACAAAATTGAAGAATGTTAATGTTCGAGTTTTCTTATCTTGTGT
                 2270                   2290                  2310
TTAGAGGTTGTTTTTTGCAGATCTTGGTGTTAATAGACCAAATAAATAAATAAATATTCCCAGCAAAAAAAAA
```

FIGURE 3

```
      -2070              -2050              -2030              -2010              -1990
tttctccctgaagtctcaatgaagaggaaataatacccatttcacaagtgtggtc ttgagcaat aaataagataaagtatgcatggtact
            -1970              -1950              -1930              -1910
taacatgtacctagcatggagaaaggaattcaatgaatattcgttgctaccattactgattttattaatgaagatgtgaggcagggtggt
      -1890              -1870              -1850              -1830              -1810
tcaatatgatgtgttagagatctgagctaggaatcaaaaggactcacttctttggacttcagtttcactacttgtaacatggtaagaatc
            -1790              -1770              -1750              -1730
catgttttcctttccagattgtcatgaggatttcttaaaagtacatgaagactttgaactacttgaaattgaggaacaatataaatgc
      -1710              -1690              -1670              -1650              -1630
aagatatcttttttcaactgagttaattaatcttataaagactgagttttaatcagttcatcaattttgtttattcttctctgtctt
            -1610              -1590              -1570              -1550
gattagattgtcctcttcatggaaaagtagtacagcatttcttcaatcaattaaaaaaacagttcaaatgtcagatcttgaagtaaatcc -1530              -1510              -1490              -1470              -1450
ttcaaaactgcaagagtacactctttgcaaagaaaacctttcttcggtatgttcc attgcctca attcattcagtgtatgtaggctaatt
            -1430              -1410              -1390              -1370
ttaatattcaacccactcttgaatttccactttgggtattatctactttcaatatttaatcccagaatgacttctctttgcctcacagca
      -1350              -1330              -1310              -1290              -1270
ggctcccagattacctcttttctctgattagttagtatggcttcagggaatatcttcttttaacattaaactgggcaaaaacagaaat -1250              -1230              -1210              -1190
agaaagaaaaatc tgtagcaag atcaaaaatagaattcacagctaaatataaatctggagggaattattcaattatttgaatggtcccca
      -1170              -1150              -1130              -1110              -1090
atcacagacaatccagggttgattgacttttgcttttccatatgtagaacaaaatggttaacaaataccaagagtaatatttttttct
            -1070              -1050              -1030              -1010
tttgaagcataatacttttaatagtatcttaaatgttatttctttcccaaatccctttatattattatatcatgtgcttttcacaact
      -990               -970               -950               -930               -910
gcatgcattctctttggggaccttccagtctcattctgacttgtaagtcagagagcattgatcttggaagaccaggatttgttaacggag -890               -870               -850               -830
tcgcggtgcaaac ttgggcaag ttttcagttgctttgttcctttcactctgctgagctagacttggagtggacgactctgaagggaaat
      -810               -790               -770               -750               -730
tccctgcttcttttcagagtcccaatttaatttacaggctagcaattgttttttaaggttggatcaacaccaagtagggacttggaaac
            -710               -690               -670               -650
gtggagaaagacagatgtaagtgtcacacgaggcaaggtcgccattaaatacacaaatataatgcaaatcacatgcaaatgatatgcaaa
      -630               -610               -590               -570               -550
ccttgcattaatttgtaggatcttagtttggagcttgtaagtagcactgagatcctataaggatttaaaactaatgttttttaggttaaa
            -530               -510               -490               -470
ttaaatgtaatactttttgaaggtatcgctttctctgtgattcagggactcaactgtgtaaagtttgacactgctccctactcccgcccc
      -450               -430               -410               -390               -370
caaaaattatttcactagtgtttgactccaacctacacccagcgccgcgcccactctccagctcagcctgacgtcacgtgacattatatt
            -350               -330               -310               -290
tgcatactacctgggactgggtgtgacgctcccctattctgcgtcttctcattggtggcgctggagaaccagccctcttctgtacaggcc
      -270               -250               -230               -210               -190
aatcagcagcccctgggatgttggaaaaccgaaggggcggtgtgagggtggggtcttggcttggatcgctaggctcatcgaccaatcat
            -170               -150               -130               -110
cctcaggaaagggaaggctaagctgtggattggctggggtggaaggtctgggtttccgcagtccaatgacagctctaggatgagggggcc
      -90                -70                -50                -30                -10
ggtccccgccccgtacagcagataagcagcggcctcgggggttgggggctgtgtgagtctcgcagtggggctgaggcaggcagccggga
      1         10                 30                 50                 70
gagcc ATG GCGGGGGCCGCAGCGGGCGGCAGAGGCGGAGGTGCCTGGGGGCCGGGGCGCGGAGGGGCCGGGGGGCTCCGGCGGGGCTGCT
      90                 110                130
CTCCCCCAGCCCCCGCCGGCTCCCCCCGGGCTGGGCTGCAGCCGCTCAGGGCCACGATCC
```

FIGURE 4

|   | 1 | 2 | 3 | 4 | 5 | 6 | 7 | 8 |
|---|---|---|---|---|---|---|---|---|
| A | whole brain | amygdala | caudate nucleus | cerebellum | cerebral cortex | frontal lobe | hippocampus | medulla oblongata |
| B | occipital lobe | putamen | substantia nigra | temporal lobe | thalamus | acumens | spinal cord | |
| C | heart | aorta | skeletal muscle | colon | bladder | uterus | prostate | stomach |
| D | testis | ovary | pancreas | pituitary gland | adrenal gland | thyroid gland | salivary gland | mammary gland |
| E | kidney | liver | small intestine | spleen | thymus | peripheral leukocyte | lymph node | bone marrow |
| F | appendix | lung | trachea | placenta | | | | |
| G | fetal brain | fetal heart | fetal kidney | fetal liver | fetal spleen | fetal thymus | fetal lung | |
| H | yeast total RNA | yeast tRNA | E. coli rRNA | E. coli DNA | Poly r(A) | human C₀t 1 DNA | human DNA | human DNA |

FIGURE 5

Hours of ATRA Treatment
0 2 4 6 24 48 90 120
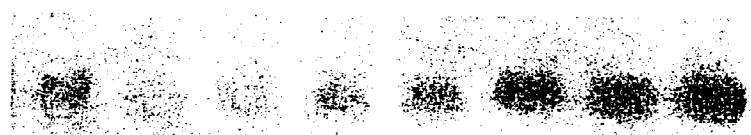
CDDP-1
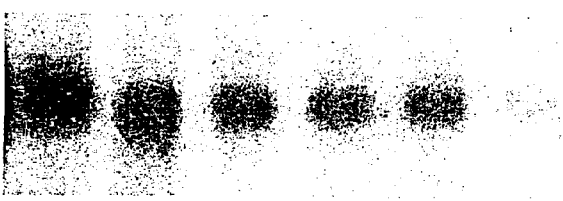
MPO
LF
C/EBPε
GAPDH
FIGURE 10

| Days of Treatment | ATRA | | | | | | PMA | | | | |
|---|---|---|---|---|---|---|---|---|---|---|---|
| | 0 | 1 | 2 | 3 | 4 | 5 | 1 | 2 | 3 | 4 | |
| | | | | | | | | | | | CDDP-1 |
| | | | | | | | | | | | c-FMS |
| | | | | | | | | | | | MPO |
| | | | | | | | | | | | C/EBPα |
| | | | | | | | | | | | C/EBPβ |
| | | | | | | | | | | | C/EBPδ |
| | | | | | | | | | | | C/EBPε |
| | | | | | | | | | | | GAPDH |

FIGURE 11

Hours of ATRA Treatment
0  2  4  8  24  48  72  96  120  144
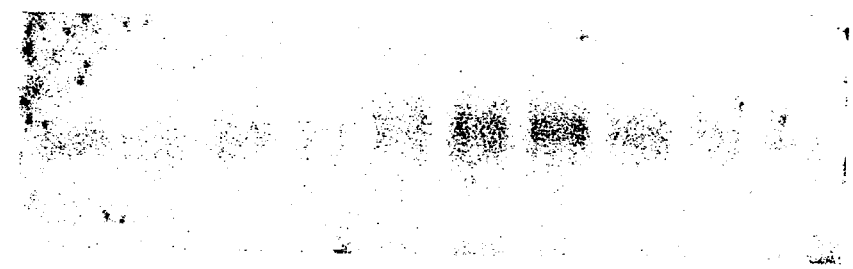 CDP-1
 MPO
 GAPDH
FIGURE 12

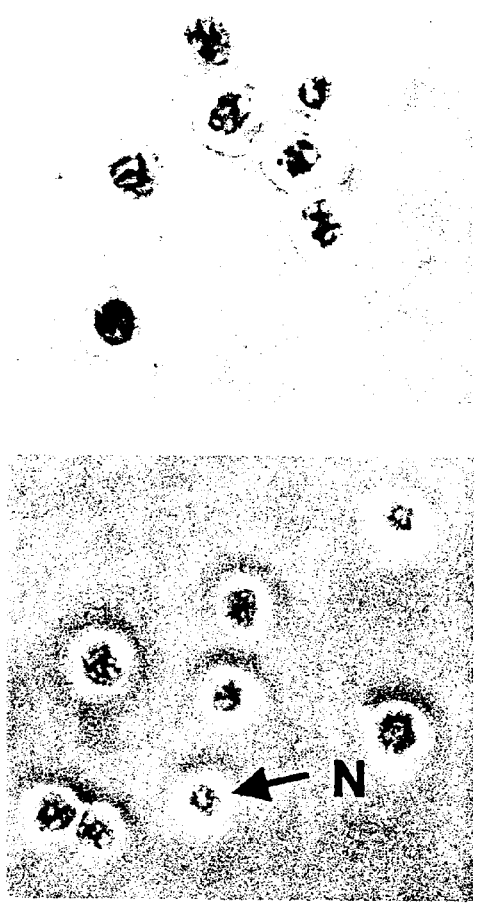 MPRO-puro
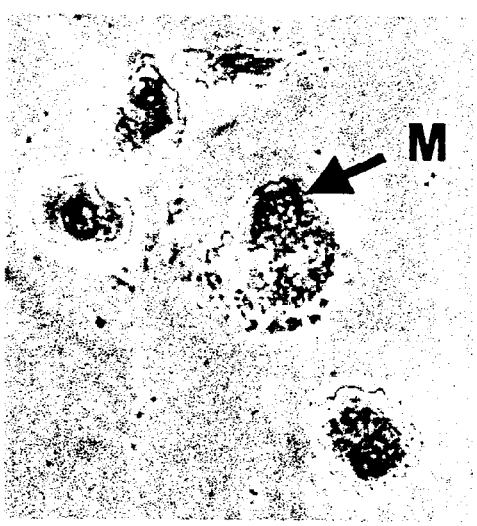 MPRO-CDDP-1 #1
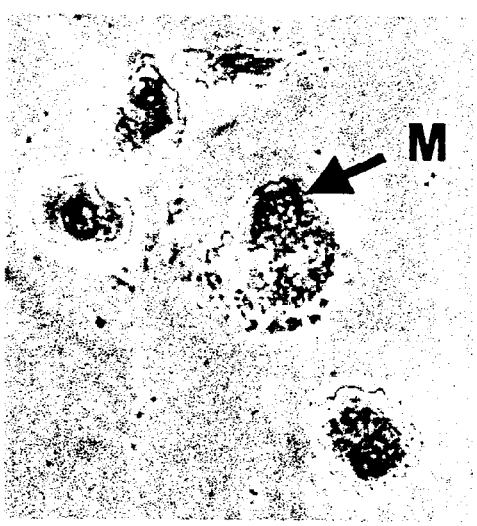 MPRO-CDDP-1 #9
FIGURE 13

MPRO-puro + ATRA        MPRO-CDDP-1 + ATRA
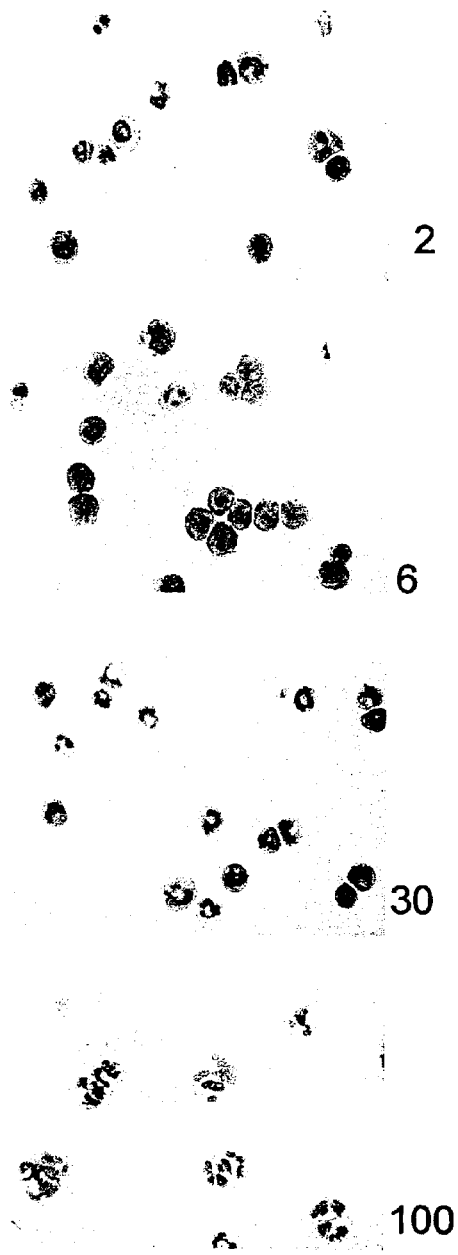
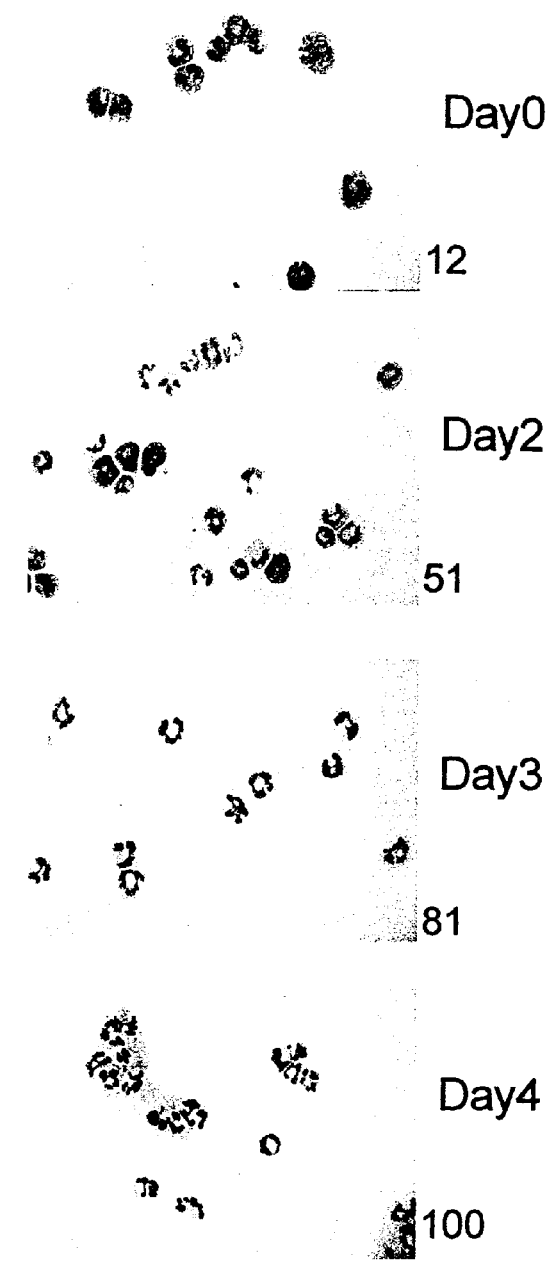
FIGURE 16

Hours of DMSO Treatment
0  2  4  10  27  72  120
 CDDP-1
 c-MYB
 β-Globin
 GAPDH
FIGURE 19

Days in Wehi-3 conditioned media
0 1 2 3 4 5 6 7
 CDDP-1
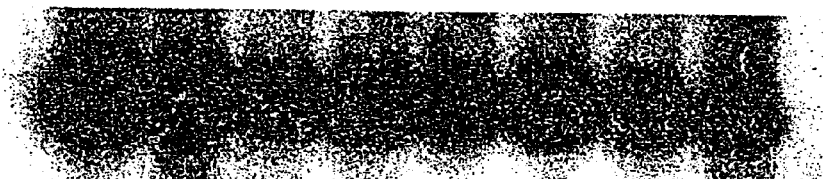 GAPDH
FIGURE 20

SEQUENCE LISTING

<160> NUMBER OF SEQ ID NOS: 3

<210> SEQ ID NO 1
<211> LENGTH: 2330
<212> TYPE: DNA
<213> ORGANISM: Homo sapiens
<220> FEATURE:
<221> NAME/KEY: CDS
<222> LOCATION: (31)..(1389)
<223> OTHER INFORMATION: open reading frame encoding CDDP-1
<221> NAME/KEY: Unsure
<222> LOCATION: (14)..(14)
<223> OTHER INFORMATION: unsure of nucleotide
<221> NAME/KEY: Unsure
<222> LOCATION: (2)..(2)
<223> OTHER INFORMATION: unsure of nucleotide

<400> SEQUENCE: 1

```
gnccctcgac ggcntgcagc cgggagagcc atg gcg ggg gcc gca gcg ggc ggc       54
                                Met Ala Gly Ala Ala Ala Gly Gly
                                 1               5 aga ggc gga ggt gcc tgg ggg ccg ggc gcg gga ggg gcc ggg ggg ctc      102
Arg Gly Gly Gly Ala Trp Gly Pro Gly Arg Gly Ala Gly Gly Leu
        10                  15                  20 cgg cgg ggc tgc tct ccc cca gcc ccc gcc ggc tcc ccc cgg gct ggg      150
Arg Arg Gly Cys Ser Pro Pro Ala Pro Ala Gly Ser Pro Arg Ala Gly
 25                  30                  35                  40 ctg cag ccg ctc agg gcc acg atc ccc ttc cag ctg cag cag ccg cac      198
Leu Gln Pro Leu Arg Ala Thr Ile Pro Phe Gln Leu Gln Gln Pro His
                 45                  50                  55 cag cgc cgg gac ggg ggt ggc cgt gca gcc agc gtc cca tgc tcg gtg      246
Gln Arg Arg Asp Gly Gly Gly Arg Ala Ala Ser Val Pro Cys Ser Val
             60                  65                  70 gcc cca gaa aag tca gtg tgt agg cct cag cca ctt cag gtc cgg cgt      294
Ala Pro Glu Lys Ser Val Cys Arg Pro Gln Pro Leu Gln Val Arg Arg
         75                  80                  85 aca ttc tcc ctg gac acc atc ctc agc tcc tac ctt ctg ggc cag tgg      342
Thr Phe Ser Leu Asp Thr Ile Leu Ser Ser Tyr Leu Leu Gly Gln Trp
     90                  95                 100 cca cga gat gct gat ggg gcc ttc acc tgc tgc acc aat gac aag gcc      390
Pro Arg Asp Ala Asp Gly Ala Phe Thr Cys Cys Thr Asn Asp Lys Ala
105                 110                 115                 120 acc cag acg ccc ctg tcc tgg caa gag cta gaa ggt gag cgt gcc agt      438
Thr Gln Thr Pro Leu Ser Trp Gln Glu Leu Glu Gly Glu Arg Ala Ser
                125                 130                 135 tcc tgt gca cac aag cgc tca gca tcc tgg ggc agc aca gac cac cga      486
Ser Cys Ala His Lys Arg Ser Ala Ser Trp Gly Ser Thr Asp His Arg
            140                 145                 150 aaa gag att tcc aag ttg aag caa caa ctg cag agg acg aag ctg agc      534
Lys Glu Ile Ser Lys Leu Lys Gln Gln Leu Gln Arg Thr Lys Leu Ser
        155                 160                 165 cgc agt ggg aaa gag aag gag cga ggt tca cca ctc tta ggg gac cac      582
Arg Ser Gly Lys Glu Lys Glu Arg Gly Ser Pro Leu Leu Gly Asp His
    170                 175                 180 gca gtg cgg gga gca ctg agg gcg tcc cct ccc agc ttc ccc tca ggg      630
Ala Val Arg Gly Ala Leu Arg Ala Ser Pro Pro Ser Phe Pro Ser Gly
185                 190                 195                 200 tcc cct gtc ttg cga ctc agc ccc tgc ctg cac agg agc ctg gaa ggg      678
Ser Pro Val Leu Arg Leu Ser Pro Cys Leu His Arg Ser Leu Glu Gly
                205                 210                 215 ctc aac caa gag ctg gag gag gta ttt gtg aag gag cag gga gaa gag      726
```

```
                Leu Asn Gln Glu Leu Glu Glu Val Phe Val Lys Glu Gln Gly Glu
                                220                 225                 230 gag ctg ctg agg atc ctt gat atc cct gat ggg cac cgg gcc cca gct      774
Glu Leu Leu Arg Ile Leu Asp Ile Pro Asp Gly His Arg Ala Pro Ala
            235                 240                 245 cct ccc cag agt ggc agc tgt gat cat ccc ctc ctc ctc ctg gag cct      822
Pro Pro Gln Ser Gly Ser Cys Asp His Pro Leu Leu Leu Leu Glu Pro
250                 255                 260 ggc aac ctt gcc agc tct cct tcc atg tcc ttg gca tct ccc cag cct      870
Gly Asn Leu Ala Ser Ser Pro Ser Met Ser Leu Ala Ser Pro Gln Pro
265                 270                 275                 280 tgt ggc ctg gcc agt cat gag gaa cat cgg ggt gcc gcc gag gag ctg      918
Cys Gly Leu Ala Ser His Glu Glu His Arg Gly Ala Ala Glu Glu Leu
                285                 290                 295 gca tcc acc ccc aac gac aaa gcc tcc tct cca gga cac cca gcc ttt      966
Ala Ser Thr Pro Asn Asp Lys Ala Ser Ser Pro Gly His Pro Ala Phe
            300                 305                 310 ctt gaa gat ggc agc cca tct cca gtc ctt gcc ttt gct gcc tcc cct     1014
Leu Glu Asp Gly Ser Pro Ser Pro Val Leu Ala Phe Ala Ala Ser Pro
        315                 320                 325 cga cct aat cat agc tac atc ttc aaa cgg gag ccc cca gaa ggc tgt     1062
Arg Pro Asn His Ser Tyr Ile Phe Lys Arg Glu Pro Pro Glu Gly Cys
    330                 335                 340 gag aaa gtg cgt gtg ttt gaa gaa gcc acg tct cca ggt cct gac ctg     1110
Glu Lys Val Arg Val Phe Glu Glu Ala Thr Ser Pro Gly Pro Asp Leu
345                 350                 355                 360 gcc ttc ctg act tcc tgt cct gac aag aac aaa gtc cat ttc aac ccg     1158
Ala Phe Leu Thr Ser Cys Pro Asp Lys Asn Lys Val His Phe Asn Pro
                365                 370                 375 act ggc tca gcc ttc tgc ccc gtc aac ctg atg aag ccc ctc ttc ccc     1206
Thr Gly Ser Ala Phe Cys Pro Val Asn Leu Met Lys Pro Leu Phe Pro
            380                 385                 390 ggc atg ggc ttc atc ttc cgt aac tgc ccc tca aac ccg gga tct ccc     1254
Gly Met Gly Phe Ile Phe Arg Asn Cys Pro Ser Asn Pro Gly Ser Pro
        395                 400                 405 ctt ccc ccg gcc agc ccc agg cca cca cct cgg aag gat ccg gaa gcc     1302
Leu Pro Pro Ala Ser Pro Arg Pro Pro Pro Arg Lys Asp Pro Glu Ala
    410                 415                 420 tcc aag gcc tcc cca ctg cca ttc gag cca tgg cag cgc acc cca cca     1350
Ser Lys Ala Ser Pro Leu Pro Phe Glu Pro Trp Gln Arg Thr Pro Pro
425                 430                 435                 440 tca gaa gag cct gtg ctt ttc cag agc tcc ctg atg gtc tgagggtccc      1399
Ser Glu Glu Pro Val Leu Phe Gln Ser Ser Leu Met Val
                445                 450 acccctgccc cactttacca tagagaccag tgccttggtg gcaggtccct ccccaggtcc   1459
cctgagatgg ggtatggagg ggcccttccc tctcggcctt cgagcacttt ctttcactta   1519
ctgtgtcaaa gccctgggtc ctcttttga tgggcaccgg cccctctgaa cgtgatggga    1579
cctgccttct ccactagtag ctgggcagct cacaattcac acctgtgtac ctgccacatc   1639
cctcacttgg tggaaaacac ccagaaggtc ttgagtcccc caccctggg tgtcagtcca    1699 aatgactgta taggaggccc ttatttttgt cacagagcaa gctggccatg aacgaaggag   1759
agaagacgcc acagatttcc ttccctctcc tccaggagac cataagatag atccccgcatc  1819 ctctcagccc tattcccatg cctccctctc attggaggag ctgaccaaag cagccctaac   1879
gggccataac acttgaccaa ttcagctgct ggcagaggga ggaaacaagt gttttcccaa   1939
gtggcatttt catctcgctt tcaccctgac taaagattgt cttaagtagc agcccagccc   1999
```

-continued

```
gcccagcccc aggtgggtag tggggaggag agctggcatt cctccaggtg gcaaatggcg    2059
actctatact ctccgcccgc cccagggctg gatggattag aaaaatccct attttcttg     2119 tatcgatgta gagactctat tttctcccaa agacactatt tttgcagctg tttgaagttt    2179
gtatattttc cgtactgcag agcttacaca aaattgaaga atgttaatgt tcgagttttc    2239
ttatcttgtg tttagaggtt gttttttgca gatcttggtg ttaatagacc aaataaataa    2299
ataaatattc ccagcaaaaa aaaaagtcga c                                   2330
```

<210> SEQ ID NO 2
<211> LENGTH: 453
<212> TYPE: PRT
<213> ORGANISM: Homo sapiens

<400> SEQUENCE: 2

```
Met Ala Gly Ala Ala Gly Gly Arg Gly Gly Ala Trp Gly Pro
1               5                   10                  15

Gly Arg Gly Gly Ala Gly Gly Leu Arg Arg Gly Cys Ser Pro Pro Ala
            20                  25                  30

Pro Ala Gly Ser Pro Arg Ala Gly Leu Gln Pro Leu Arg Ala Thr Ile
        35                  40                  45

Pro Phe Gln Leu Gln Gln Pro His Gln Arg Arg Asp Gly Gly Gly Arg
    50                  55                  60

Ala Ala Ser Val Pro Cys Ser Val Ala Pro Glu Lys Ser Val Cys Arg
65                  70                  75                  80

Pro Gln Pro Leu Gln Val Arg Arg Thr Phe Ser Leu Asp Thr Ile Leu
                85                  90                  95

Ser Ser Tyr Leu Leu Gly Gln Trp Pro Arg Asp Ala Asp Gly Ala Phe
            100                 105                 110

Thr Cys Cys Thr Asn Asp Lys Ala Thr Gln Thr Pro Leu Ser Trp Gln
        115                 120                 125

Glu Leu Glu Gly Glu Arg Ala Ser Ser Cys Ala His Lys Arg Ser Ala
    130                 135                 140

Ser Trp Gly Ser Thr Asp His Arg Lys Glu Ile Ser Lys Leu Lys Gln
145                 150                 155                 160

Gln Leu Gln Arg Thr Lys Leu Ser Arg Ser Gly Lys Glu Lys Glu Arg
                165                 170                 175

Gly Ser Pro Leu Leu Gly Asp His Ala Val Arg Gly Ala Leu Arg Ala
            180                 185                 190

Ser Pro Pro Ser Phe Pro Ser Gly Ser Pro Val Leu Arg Leu Ser Pro
        195                 200                 205

Cys Leu His Arg Ser Leu Glu Gly Leu Asn Gln Glu Leu Glu Glu Val
    210                 215                 220

Phe Val Lys Glu Gln Gly Glu Glu Leu Leu Arg Ile Leu Asp Ile
225                 230                 235                 240

Pro Asp Gly His Arg Ala Pro Ala Pro Pro Gln Ser Gly Ser Cys Asp
                245                 250                 255

His Pro Leu Leu Leu Glu Pro Gly Asn Leu Ala Ser Pro Ser
            260                 265                 270

Met Ser Leu Ala Ser Pro Gln Pro Cys Gly Leu Ala Ser His Glu Glu
        275                 280                 285

His Arg Gly Ala Ala Glu Glu Leu Ala Ser Thr Pro Asn Asp Lys Ala
    290                 295                 300

Ser Ser Pro Gly His Pro Ala Phe Leu Glu Asp Gly Ser Pro Ser Pro
305                 310                 315                 320
```

```
Val Leu Ala Phe Ala Ala Ser Pro Arg Pro Asn His Ser Tyr Ile Phe
                325                 330                 335

Lys Arg Glu Pro Pro Glu Gly Cys Glu Lys Val Arg Val Phe Glu Glu
            340                 345                 350

Ala Thr Ser Pro Gly Pro Asp Leu Ala Phe Leu Thr Ser Cys Pro Asp
        355                 360                 365

Lys Asn Lys Val His Phe Asn Pro Thr Gly Ser Ala Phe Cys Pro Val
    370                 375                 380

Asn Leu Met Lys Pro Leu Phe Pro Gly Met Gly Phe Ile Phe Arg Asn
385                 390                 395                 400

Cys Pro Ser Asn Pro Gly Ser Pro Leu Pro Ala Ser Pro Arg Pro
                405                 410                 415

Pro Pro Arg Lys Asp Pro Glu Ala Ser Lys Ala Ser Pro Leu Pro Phe
            420                 425                 430

Glu Pro Trp Gln Arg Thr Pro Pro Ser Glu Glu Pro Val Leu Phe Gln
        435                 440                 445

Ser Ser Leu Met Val
    450

<210> SEQ ID NO 3
<211> LENGTH: 3000
<212> TYPE: DNA
<213> ORGANISM: Homo sapiens
<220> FEATURE:
<221> NAME/KEY: misc_feature
<222> LOCATION: (2896)..(2899)
<223> OTHER INFORMATION: start codon for CDDP-1

<400> SEQUENCE: 3
ctttagctat accacctcca ctgcctcttt ttctaccgtc caggttctta atttctggta      60
ccttggcttt ggaataaagt ttaaacacag tatccatgga accatgcaca ttactcctct     120
ctctgaggga aggaagcatc tgtacgataa tgtgtcgcct tattttttaga acaagtctgt    180 gaggttgatg gagcagggat gattctggca cagagagagg aagccactta cccaaagtgt    240
ttcaagattc tcatcctagg gctttacttc taaacacaca ttgtctggct cagccaataa    300
aaaccactca tcatctccta agattgagaa tttacatgtt gagggtcct aacacagtat    360 aagttgtcag acaagaaaag ctttcaaaag accaactagt ctaccttttg cctctcaggc    420
aggaccaatg atctagaagt tgagtgttgg ttgggaaagc attgaatctg gagtcaaaag    480
accaaggatg taagtcctag gtctgccatt tactaagatg atcttgggca agtcacctag    540
cctctgtagg acttaacctc ctgaagaatg aggacaataa tatctacatt ttctgcctta    600
catgcctatt gtgataatta aatgagataa tgtatgtgaa agctataaaa cactagacag    660
atgttaattt taacatctta atcagatttg catctttgga gaccctttat gtaagatgtg    720
aacagtaatc ctgtgttctt aagaaaattt tacactcata gagatcagga gctcagctct    780
ggagtcaggc tacctgggta atcttgggca tgttactgta tttctccctg aagtctcaat    840
gaagaggaaa taatacccat ttcacaagtg tggtcttgag caataaataa gataaagtat    900
gcatggtact taacatgtac ctagcatgga gaaaggaatt caatgaatat tcgttgctac    960
cattactgat tttattaatg aagatgtgag gcagggtggt tcaatatgat gtgttagaga   1020
tctgagctag gaatcaaaag gactcacttc tttggacttc agtttcacta cttgtaacat   1080
ggtaagaatc catgtttttc cttttccaga ttgtcatgag gatttcttaa aagtacatga   1140
agactttgaa ctacttgaaa ttgaggaaca atataaatgc aagatatctt ttttcaactg   1200
```

```
agttaattaa tcttataaag actgagtttt taatcagttc atcaattttt gtttattctt    1260
ctctgtcttt gattagattg tcctcttcat ggaaaagtag tacagcattt cttcaatcaa    1320
ttaaaaaaac agttcaaatg tcagatcttg aagtaaatcc ttcaaaactg caagagtaca    1380
ctctttgcaa agaaaacctt tcttcggtat gttccattgc ctcaattcat tcagtgtatg    1440
taggctaatt ttaatattca acccactctt gaatttccac tttgggtatt atctactttc    1500
aatatttaat cccagaatga cttctctttg cctcacagca ggctcccaga ttacctcttt    1560
ttctctgatt agttagtatg gcttcaggga atatcttctt tttaacatta aactgggcaa    1620
aaacagaaat agaaagaaaa atctgtagca agatcaaaaa tagaattcac agctaaatat    1680
aaatctggag ggaattattc aattatttga atggtccca atcacagaca atccagggtt    1740
gattgacttt tgctttttcc atatgtagaa caaaatggtt aacaaatacc aagagtaata    1800
ttttttttct tttgaagcat aatactttt aatagtatct taaatgttat tttctttccc     1860
aaatcccttt atattattat atcatgtgct tttcacaact gcatgcattc tctttgggga    1920
ccttccagtc tcattctgac ttgtaagtca gagagcattg atcttggaag accaggattt    1980
gttaacggag tcgcggtgca aacttgggca agtttttcag ttgctttgtt cctttcactc    2040
tgctgagcta gacttggagt ggacgactct gaagggaaat tccctgcttc ttttcagagt    2100
cccaatttaa tttacaggct agcaattgtt tttttaaggt tggatcaaca ccaagtaggg    2160
acttggaaac gtggagaaag acagatgtaa gtgtcacacg aggcaaggtc gccattaaat    2220
acacaaatat aatgcaaatc acatgcaaat gatatgcaaa ccttgcatta atttgtagga    2280
tcttagtttg gagcttgtaa gtagcactga gatcctataa ggatttaaaa ctaatgtttt    2340
ttaggttaaa ttaaatgtaa tactttttga aggtatcgct ttctctgtga ttcagggact    2400
caactgtgta aagtttgaca ctgctcccta ctcccgcccc caaaaattat ttcactagtg    2460
tttgactcca acctacaccc agcgccgcgc ccactctcca gctcagcctg acgtcacgtg    2520
acattatatt tgcatactac ctgggactgg gtgtgacgct cccctattct gcgtcttctc    2580
attggtggcg ctggagaacc agccctcttc tgtacaggcc aatcagcagc ccctgggatg    2640
ttggaaaacc gaagggggcg gtgtgagggt ggggtcttgg cttggatcgc taggctcatc    2700
gaccaatcat cctcaggaaa gggaaggcta agctgtggat tggctggggt ggaaggtctg    2760
ggtttccgca gtccaatgac agctctagga tgagggggcc ggtccccgcc ccgtacagca    2820
gataagcagc ggcctcgggg gttgggggc tgtgtgagtc tcgcagtggg gctgaggcag     2880
gcagccggga gagccatggc gggggccgca gcgggcggca gaggcggagg tgcctggggg    2940
ccggggcgcg gagggccgg ggggctccgg cggggctgct ctccccagc cccgccggc       3000
```

GENE WHOSE EXPRESSION PROMOTES DIFFERENTIATION OF MYELOID PROGENITOR CELLS INTO NEUTROPHILS AND/OR MONOCYTES/MACROPHAGES

CROSS-REFERENCE TO RELATED APPLICATION

Not applicable.

STATEMENT REGARDING FEDERALLY SPONSORED RESEARCH OR DEVELOPMENT

Not Applicable.

BACKGROUND OF THE INVENTION

(1) Field of the Invention

The present invention relates to a human gene sequence that encodes the CDDF-1 polypeptide, which is involved in cell differentiation, in particular differentiation of undifferentiated or immature cells into neutrophils, monocytes/macrophages, mast cells and/or erythroid cells. The present invention further relates to assays for detecting CDDP-1 expression, vectors that express CDDP-1, methods for using CDDP-1 to induce or promote cell differentiation, and transgenic animals deficient in one or both CDDP-1 alleles. The present invention further relates to methods of gene therapy which comprise the administration of the above vectors to a human or animal.

(2) Description of Related Art

Development in higher eukaryotes proceeds by the differential, temporal, and tissue specific expression of particular genes. Among the factors which control gene expression are positive transcription factors that increase gene expression by binding to specific DNA sequences called enhancer sequences. These factors are called enhancer binding proteins. One such family of enhancer binding proteins is the CCAAT/enhancer binding protein (C/EBP) family.

The C/EBP family of transcription factors has been implicated in both the regulation of differentiation and differentiated function in myelomonocytic cells. C/EBPα, C/EBPβ, and C/EBPδ are temporally regulated in the granulocyte-colony stimulating factor (G-CSF)-stimulated differentiation of 32D clone 3 myeloblasts into granulocytes (Scott et al., Blood 80: 1725–1735 (1992)). C/EBPα is expressed at high levels early in differentiation and decreases to an undetectable level in terminally differentiated cells, while C/EBPβ and C/EBPδ are upregulated as the cells differentiate.

Similarly, C/EBPβ is upregulated in macrophage differentiation (Natsuka et al., Blood 79: 460–466 (1992)). However, observations in primary cells and in bipotential precursor cell lines yield a somewhat different pattern of C/EBPα expression (Radomska et al., Mol. Cell. Biol. 18: 4301–4314 (1998)). In these cell lines, C/EBPα is first expressed when multipotential cells become committed to the myeloid lineage, then C/EBPα expression is upregulated and its expression maintained during granulocytic expression, then its expression is rapidly down regulated during monocytic differentiation. Consistent with its early appearance and high level of expression in granulocyte differentiation, conditional expression of C/EBPα in transfected bipotential cells induces neutrophilic differentiation and blocks monocytic differentiation (Radomska et al. ibid.). C/EBPα has been shown to induce expression of the G-CSF receptor and the interleukin-6 (IL-6) receptor. Both receptors are involved in cell development.

Genetically created C/EBPα-deficient mice are completely blocked in the development of neutrophils and eosinophils (Zhang et al., Proc. Natl. Acad. Sci. USA 94: 569 (1997)). While these mice no longer express the C/EBPα-regulated G-CSF receptor, lack of G-CSF expression alone is not responsible for the blocked development because mice deficient in G-CSF receptor expression are still capable of producing mature neutrophils, albeit in numbers that are reduced compared to that in normal mice (Liu et al., Immunity 5: 491–501 (1996)). The IL-6 receptor is either directly or indirectly regulated by C/EBPα, and IL-6 signaling is important for granulopoiesis; however, the genetically created IL-6 receptor and the G-CSF receptor deficient mice are similar to mice made deficient for only the G-CSF receptor (Zhang et al., J. Exp. Med. 188: 1173–1184 (1998)). Therefore, there must be other important C/EBPα genes other than those encoding the G-CSF receptor and the IL-6 receptor.

Consistent with peak expression late in myeloid differentiation, C/EBPβ and C/EBPδ are effectors in the induction of proinflammatory genes responsible for LPS, IL-1, or IL-6 stimulation (Akira et al., EMBO J. 9: 1897–1906 (1990); Kinoshita et al., Proc. Natl. Acad. Sci. USA 89: 1473–1476 (1992)). The DNA binding activity of C/EBPβ is increased by a post-transcriptional mechanism when cells are exposed to LPS, IL-1, or IL-6 (Akira et al. ibid.; Poli et al., Cell 63: 643–653 (1990)), and C/EBPβ and C/EBPδ mRNA levels can be induced by LPS, IL-1, or IL-6 (Akira et al. ibid.; Kinoshita et al. ibid.). C/EBPβ expression is capable of enhancing transcription from promoters containing elements responsive to those factors (Akira et al. ibid.; Poli et al. ibid.; Chang et al., Mol. Cell. Biol. 10: 6642–6653 (1990); Descombes et al., Genes Dev. 4: 1541–1551 (1990)). Both C/EBPβ and C/EBPδ can transactivate a reporter gene regulated by the IL-6 promoter in transient assays (Akira et al. ibid.; Kinoshita et al. ibid.). Furthermore, the promoter regions of the genes for IL-6, IL-1α, IL-1β, IL-8, tumor necrosis factor alpha (TNFβ), G-CSF, macrophage inducible nitric oxide synthase (iNOS), and lysozyme (Akira et al. ibid.; Furutani et al., Nuc. Acids Res. 14: 3167–3179 (1986); Lowenstein et al., Proc. Natl. Acad. Sci. USA 90: 9730–9734 (1993); Natsuka et al., Blood 79: 460–466 (1992); Shirakawa et al., Mol. Cell. Biol. 13: 1332–1344 (1993); Zhang and Rom, Mol. Cell. Biol. 13: 3831–3837 (1993)) all contain C/EBP binding motifs. Furthermore, ectopic expression of C/EBPα, C/EBPβ, or C/EBPδ confers LPS-inducibility of IL-6 and MCP-1 expression to cell lines that normally lack C/EBP expression (Bretz et al., Proc. Natl. Acad. Sci. USA 91: 7306–7310 (1994); Hu et al., J. Immunol. 160: 2334–2342 (1998)).

C/EBPε is unique among the transcription factors of the C/EBP family because it is myeloid-specific in its expression (Williams et al., J. Biol. Chem. 273: 13493–13501 (1998); Chumakov et al., Mol. Cell. Biol. 17: 1375–1386 (1997)). In particular, C/EBPε is expressed in maturing neutrophils (Chih et al., Blood 90: 2987–2994 (1997); Morosetti et al., Blood 90: 2591–2600 (1997); Yamanaka et al., Proc. Natl. Acad. Sci. USA 94: 6462–6467 (1997)). C/EBPε-deficient mice fail to develop functional neutrophils and eosinophils (Yamanaka et al., Proc. Natl. Acad. Sci. USA 94: 13187–13192 (1997)) with a block later in the differentiation process than that seen in C/EBPα-deficient mice. Consistent with a block later in the differentiation process, C/EBPε has been found to transactivate, in cooperation with c-myb, the promoters for mim-1 and neutrophil elastase in transient expression assays (Verbeek et al., Blood 93: 3327–3337 (1999)), and to upregulate endogenous expression of a number of genes encoding proinflammatory cytokines including IL-6, MCP-1, MIP-1α, and MIP-1β (Williams et al. ibid.).

C/EBP family members have also been implicated in the differentiation of the erythroid and B cell lineages. Erythropoietin upregulates expression of CHOP, a C/EBP family member that acts as a dominant negative regulator of other C/EBP family members (Coutts et al., Blood 93: 3369–3378 (1999)). Overexpression of CHOP in Rauscher cells enhanced erythropoietin and DMSO-induced differentiation, while inhibition of CHOP expression reduced CFU-E formation. C/EBPβ is also upregulated in the course of erythroid differentiation. Mice deficient in C/EBPβ expression are impaired in the generation of bone marrow B lymphocytes (Chen et al., Blood 90: 156–164 (1997)). These mice showed decreased expression of IL-7 by bone marrow stromal cells as well as defective IL-7 signaling. C/EBPβ has also been shown to be a component of a DNA binding complex that activates the Id1 gene, a negative regulator of differentiation in pro-B cells (Saisanit and Sun, Mol. Cell. Biol. 17: 844–850 (1997)). This suggests that C/EBPβ participates in blocking differentiation and promoting proliferation at the pro-B cell stage, but promotes differentiation through the IL-7 pathway at later stages of differentiation.

Thus, the C/EBP family of transcription factors are important in hematopoietic differentiation and have a particularly central role in myelomonocytic differentiation. Since the currently identified target genes of C/EBP regulation seem inadequate to fully explain the role of these transcription factors in myelomonocytic differentiation, there is a need to identify other genes which have an important role in differentiation. These genes would provide tools which could be used in gene therapy or other therapeutic treatments to induce differentiation in abnormal cells that are undifferentiated such as those cells found in leukemias.

SUMMARY OF THE INVENTION

The present invention provides a human gene sequence that encodes the CDDP-1 polypeptide, which is involved in cell differentiation, in particular differentiation of undifferentiated or immature cells into neutrophils, monocytes/macrophages, mast cells and/or erythroid cells. The present invention further provides assays for detecting CDDP-1 expression, vectors that express CDDP-1, methods for using CDDP-1 to induce or promote cell differentiation, and transgenic animals deficient in one or both CDDP-1 alleles. The present invention further pertains to methods of gene therapy that comprise the administration of vectors expressing CDDP-1 to a human or animal, and for treatment of diseases that are a result of proliferation of undifferentiated cells including, but not limited to myeloid progenitor cells.

Thus, the present invention provides an isolated DNA molecule that encodes human C/EBP Differential Display Product-1 (CDDP-1) or mutant thereof wherein the CDDP-1 promotes differentiation of undifferentiated cells along a pathway of differentiation. In particular, an isolated DNA molecule that encodes human C/EBP Differential Display Product-1 (CDDP-1) or mutant thereof wherein the CDDP-1 promotes differentiation of myeloid progenitor cells along a neutrophilic, monocytic, or macrophage differentiation pathway; or an isolated DNA molecule that encodes human C/EBP Differential Display Product-1 (CDDP-1) or mutant thereof wherein the CDDP-1 promotes differentiation of hematopoietic cells along an erythroid or mast cell differentiation pathway. Most particularly, an isolated DNA molecule that encodes human C/EBP Differential Display Product-1 (CDDP-1) or mutant thereof wherein the CDDP-1, which is localized to the cytoplasm, promotes differentiation of myeloid progenitor cells into cells selected from the group consisting neutrophils, monocytes, macrophages, and combinations thereof wherein induction of CDDP-1 in neutrophilic differentiation is biphasic occurring with myeloperoxidase induction and then again with lactoferrin induction and expression of CDDP-1 in monocyte differentiation displays a pattern of reduced expression. In particular, the isolated DNA molecule wherein the expressed CDDP-1 comprises the amino acid sequence represented by SEQ ID NO:2 or mutant thereof, or wherein the DNA molecule encoding CDDP-1 comprises the nucleic acid sequence represented by SEQ ID NO:1 or mutant thereof. Thus, in a preferred embodiment, the present invention provides an isolated human DNA encoding CDDP-1 comprising the nucleotide sequence set forth in SEQ ID NO:1 or mutant thereof. In a further preferred embodiment, the DNA molecule is detectably labeled. Further still, the present invention provides an isolated CDDP-1 protein comprising the amino acid sequence set forth in SEQ ID NO:2.

The present invention also provides a vector, preferably a vector comprising a retrovirus or plasmid, comprising a DNA molecule that encodes human C/EBP Differential Display Product-1 (CDDP-1) or mutant thereof wherein the CDDP-1 promotes differentiation of undifferentiated cells along a pathway of differentiation. In particular, a vector comprising a DNA molecule that encodes human C/EBP Differential Display Product-1 (CDDP-1) or mutant thereof wherein the CDDP-1 promotes differentiation of myeloid progenitor cells along a neutrophilic, monocytic, or macrophage differentiation pathway; a vector comprising a DNA molecule that encodes human C/EBP Differential Display Product-1 (CDDP-1) or mutant thereof wherein the CDDP-1 promotes differentiation of hematopoietic cells along an erythroid or mast cell differentiation pathway; or, a DNA molecule encoding a human C/EBP Differential Display Product-1 (CDDP-1) or mutant thereof, which is involved in differentiation of myeloid progenitor cells into cells selected from the group consisting of neutrophils, monocyte, macrophages and combinations thereof. In particular, the vector wherein the encoded CDDP-1 comprises the amino acid sequence of SEQ ID NO:2 or mutant thereof or wherein the CDDP-1 is encoded by the DNA molecule comprising the nucleic acid sequence of SEQ ID NO:1 or mutant thereof. Preferably, the present invention provides a vector wherein the CDDP-1 is capable of inducing differentiation of mammalian cells. Particularly, wherein the mammalian cells comprises myeloid progenitor cells. In a preferred embodiment, the vector contains DNA comprising the nucleotide sequence set forth in SEQ ID NO:1 or mutant thereof.

The present invention also provides a cell line harboring a vector containing DNA comprising the nucleotide sequence set forth in SEQ ID NO:1 or mutant thereof. The present invention also provides a transgenic animal which is heterozygous or homozygous CDDP-1 deficient. Preferably, the transgenic animal is a mouse.

The present invention further provides a method for determining whether cells express mRNA encoding C/EBP Differential Display Product-1 (CDDP-1), which comprises (a) providing a detectably labeled nucleic acid probe complementary to the mRNA encoding CDDP-1, (b) isolating the mRNA from the cells, (c) hybridizing the probe to the isolated RNA, and (d) detecting the probe hybridized to the mRNA. In particular, the method wherein the cells comprise myeloid progenitor cells. Preferably, the probe comprises the nucleotide sequence represented in SEQ ID NO.1 or mutant thereof.

The present invention further still provides a method for determining whether cells express C/EBP Differential Display Product-1 (CDDP-1), which comprises (a) providing a detectably labeled antibody that binds the CDDP-1, (b) isolating proteins from the cells, (c) reacting the proteins with the antibody, and (d) detecting the antibody bound to the CDDP-1. In particular, the method wherein the cells comprise myeloid progenitor cells. Preferably, the CDDP-1 comprises the amino acid sequence represented in SEQ ID NO.2 or mutant thereof.

In a method further still, the present invention provides a method for regulating differentiation of cells, which comprises (a) transfecting a vector containing an isolated DNA comprising the nucleotide sequence set forth in SEQ ID NO:1 or mutant thereof encoding CDDP-1 in the cells, and (b) inducing the cells to produce the CDDP-1 to regulate the differentiation of the cells. In particular, a method wherein the cells which produce CDDP-1 are in a mammal and wherein the cells are cultured in vitro.

Further still, the present invention provides a method for testing a chemical agent to determine its effect on cells that express CDDP-1, which comprises (a) culturing cells transfected with a vector containing DNA encoding CDDP-1 as set forth in SEQ ID NO:1 or mutant thereof encoding CDDP-1, (b) introducing the chemical agent into the culture of the cells, and (c) determining the affect of the chemical agent on the cells. In particular, wherein the effect on the cells that is determined, is differentiation of the cells. Preferably, the cells are myeloblast cells. In particular, the method wherein the cells are myeloid leukemic cells or progenitor myeloid progenitor cells. In one embodiment, the chemical agent is retinoic acid. Preferably, in determining the effect, the method includes control cells that do not express CDDP-1.

Further still, the present invention provides a method for inducing or promoting differentiation of undifferentiated cells in a mammal, which comprises introducing a vector containing DNA encoding CDDP-1 protein into the undifferentiated cells of the mammal to induce or promote differentiation of the undifferentiated cells. Preferably, a method for inducing cell differentiation in a mammal, which comprises introducing a vector containing DNA comprising the nucleotide sequence set forth in SEQ ID NO:1 or mutant thereof encoding CDDP-1 into the cells of the mammal. In a particular embodiment, a chemical agent is introduced into the animal with the vector to further augment the effects produced through the production of CDDP-1 encoded by the DNA, preferably the chemical agent is retinoic acid. Preferably, the CDDP-1 comprises the amino acid sequence set forth in SEQ ID NO:2. In a preferred embodiment, the undifferentiated cells are myeloid cells.

Further still, the present invention provides a kit for determining whether cells express C/EBP Differential Display Product-1 (CDDP-1). The kit comprises (a) providing a detectably labeled antibody that binds the CDDP-1, and (b) a means for determining the amount of the antibody bound to the CDDP-1. In particular, wherein the cells comprise myeloid progenitor cells and wherein the CDDP-1 comprises the amino acid sequence represented in SEQ ID NO.2 or mutant thereof. Alternatively, the present invention provides a kit for determining the level of CDDP-1 produced by a cell, which comprises (a) a protein binding reagent, which forms a complex with the CDDP-1, and (b) means for determining the level of the reagent or CDDP-1 in the complex. In particular wherein the cells are leukemic.

Further still, the present invention provides a kit for determining whether cells express RNA encoding C/EBP Differential Display Product-1 (CDDP-1). The kit comprises (a) providing a detectably labeled nucleic acid probe that hybridizes the RNA encoding CDDP-1, and (b) a means for detecting the probe hybridized to the RNA encoding CDDP-1. In particular, wherein the cells comprise myeloid cells and wherein the nucleic acid probe comprises the nucleic acid sequence represented in SEQ ID NO.1 or mutant thereof.

Finally, the present invention provides a transgenic animal wherein the transgenic animal is heterozygous or homozygous CDDP-1 deficient. Preferably, the transgenic animal is a transgenic mouse that is deficient for one or both CDDP-1 alleles.

OBJECTS

An object of the present invention is to provide a polypeptide and a nucleic acid encoding the polypeptide wherein the polypeptide is involved in the differentiation of myeloid progenitor cells, in particular leukemia cells.

Another object of the present invention is to provide a method for identifying chemical agents that effect differentiation of myeloid cells by inducing expression of CDDP-1.

A further object of the present invention is to provide a method for inducing differentiation of leukemia cells in a patient.

These and other objects of the present invention will become increasingly apparent with reference to the following drawings and preferred embodiments.

DESCRIPTION OF THE DRAWINGS

FIG. 3 shows the nucleic acid sequence (SEQ ID NO:1) and the deduced amino acid sequence (SEQ ID NO:2) of CDDP-1.

FIG. 4 shows the approximate 2 kb upstream sequence of CDDP-1 (SEQ ID NO.3) contains four copies of putative C/EBP binding sites (boxed regions). The adenine residue of the first ATG codon in the CDDP-1 open reading frame was arbitrarily numbered +1.

FIG. 5 shows hybridization of the CDDP-1 cDNA to an RNA dot blot of RNAs from several human tissues (Clontech RNA Master Blot). The blot shows that CDDP-1 is expressed most highly in fetal liver (FL) and adult bone marrow (BM) as would be expected of a gene with a function in hematopoiesis.

FIG. 10 shows a Northern blot of RNA isolated from a time course of all trans retinoic acid (ATRA)-induced differentiation of MPRO cells. The blot was successively hybridized with nucleic acid probes for CDDP-1, myeloperoxidase (MPO), lactoferrin (LF), C/EBPε, and glyceraldehyde-3-phosphate dehydrogenase (GAPDH).

FIG. 11 shows a Northern blot of RNA isolated from time courses of all trans retinoic acid (ATRA)-induced differentiation and PMA-induced differentiation of HL-60 cells. The blot was successively hybridized with nucleic acid probes for CDDP-1, c-fms, myeloperoxidase (MPO), lactoferrin (LF), C/EBPα, C/EBPβ, C/EBPδ, C/EBPε, and glyceraldehyde-3-phosphate dehydrogenase (GAPDH).

FIG. 12 shows a Northern blot of RNA isolated from a time course of ATRA-induced differentiation of EML-C1 cells. The blot was successively hybridized with nucleic acid probes for CDDP-1, myeloperoxidase (MPO), and glyceraldehyde-3-phosphate dehydrogenase (GAPDH).

FIG. 13 shows a representative series of photomicrographs showing Wright Giemsa staining of representative CDDP-1 transductants of MPRO cells with either neutrophilic (N) or monocytic (M) morphology. MPRO-puro represents transductants infected with a control retrovirus.

FIG. 16 shows Wright Giemsa staining of a population of control MPRO cells and a population of CDDP-1 MPRO transductants over a time course of differentiation after treatment with ATRA. The number at the lower right corner of each figure represents the percentage of mature band form and polymorphonuclear cells. The examples shown are representative.

FIG. 19 shows a Northern blot of RNA isolated from a time course of DMSO-induced differentiation of BB88 cells. The blot was successively hybridized with nucleic acid probes for CDDP-L, β-globin, and glyceraldehyde-3-phosphate dehydrogenase (GAPDH).

FIG. 20 shows a Northern blot of RNA isolated from a time course of IL-3-induced mast cell differentiation of EML-C1 cells. The blot was successively hybridized with nucleic acid probes for CDDP-1 and glyceraldehyde-3-phosphate (GAPDH).

DETAILED DESCRIPTION OF THE INVENTION

Figure 1:
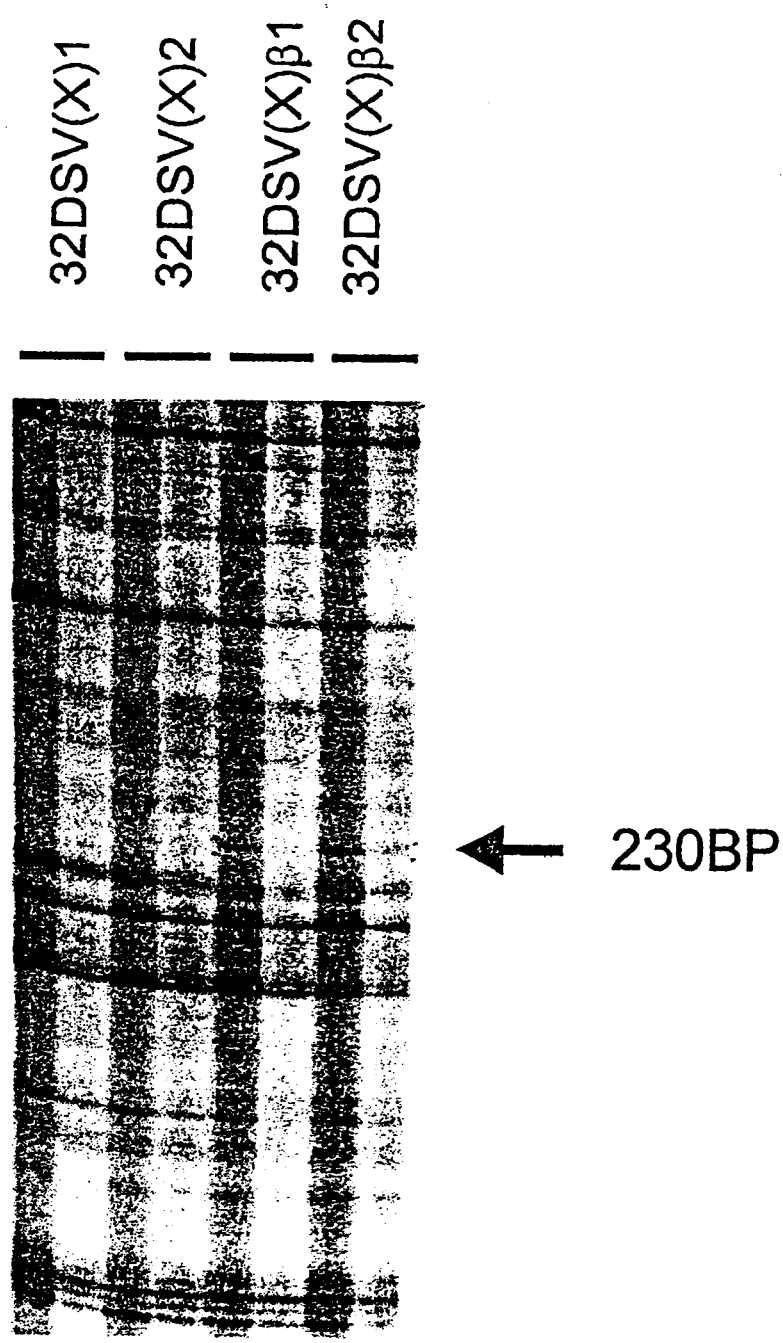
FIG. 1 shows a differential display between control and C/EBPβ-overexpressing cells. Two control populations (32DSV(X)1 and 2) and two C/EBPβ overexpressing populations (32DSVβ1 and β2) were examined at two concentrations of initial cDNA products.

All patents, patent applications, and literature references cited in this specification are hereby incorporated herein by reference in their entirety. In case of conflict, the present description, including definitions, will control.

As used herein, the term "undifferentiated cells" includes immature cells, progenitor cells, cancer cells, stem cells, and pluripotent germ cells. Such cells include, but are not limited to, immature or progenitor hematopoietic cells, promyeloblasts, promyelocytic leukemia cells, erythroleukemic cells, histiocytic lymphoma cells, and bipotential late myeloblasts.

The present invention provides a human C/EBP Differential Display Product-1 (CDDP-1) polypeptide, the nucleic acid encoding the CDDP-1, and vectors that express CDDP-1 for therapeutic treatments for particular diseases that are caused by proliferation of undifferentiated cells. CDDP-1 is a novel cytoplasmic protein, which has little structural or functional relationship to any proteins of known function. The CDDP-1 polypeptide is represented by the amino acid sequence shown in FIG. 3 (SEQ ID NO:2) or mutant thereof. The mutant amino acid sequence can comprise amino acid mutations, substitutions or deletions, that do not significantly abrogate the in vivo activity of CDDP-1, but can include mutations, substitutions or deletions, that enhance the activity of CDDP-1. The nucleic acid encoding human CDDP-1 has been isolated from a human bone marrow cDNA library and has the nucleic acid sequence represented by the nucleic acid sequence shown FIG. 3 (SEQ ID NO:1) or mutant thereof. The mutant nucleic acid sequence can comprise nucleic acid mutations, substitutions or deletions, that do not significantly abrogate the in vivo activity of the encoded CDDP-1, and can include mutations, substitutions or deletions, that enhance the activity of the encoded CDDP. The genomic DNA encoding CDDP-1 has been localized to human chromosome 17, the nucleic acid sequence of which comprises parts of the nucleic acid sequence set forth in GenBank Accession No. AC015795. A comparison of the cDNA encoding CDDP-1 (derived from the mRNA encoding CDDP-1) and the genomic DNA encoding CDDP-1 showed that the CDDP-1 gene comprises eight coding sequences (exons) separated by seven non-coding intervening sequences (introns).

CDDP-1 mRNA expression displays a biphasic pattern of expression in the granulocytic differentiation of myeloid progenitor cell lines: an early period of elevated CDDP-1 mRNA expression, which is just prior to and continuing through the induction of myeloperoxidase mRNA expression (FIGS. 9 and 12), and a later second period of CDDP-1 mRNA expression that coincides with expression of lactoferrin mRNA (FIG. 10). This pattern of CDDP-1 mRNA expression, coupled with the finding that CDDP-1 is most highly expressed in adult bone marrow and fetal liver (FIG. 5), suggests that CDDP-1 has a role in myelopoiesis. Consistent with a role in myelopoiesis, overexpression of CDDP-1 mRNA in MPRO promyelocytes promoted their differentiation along either the neutrophil or the monocyte/macrophage pathway.

The protein structure of CDDP-1 displays little homology to the structure of other proteins of known function. Because CDDP-1 is a cytoplasmic protein (FIG. 8), it is unlikely CDDP-1 is directly involved in regulation of transcription. CDDP-1 mRNA expression was upregulated in several cell lines (such as EML-C1, MPRO, HL-60, and U937) when the cell lines were induced to differentiate by treatment with retinoic acid. Also, when CDDP-1 mRNA was overexpressed in MPRO cells, it facilitated retinoic acid-induced differentiation of the MPRO cells into neutrophils (FIG. 16). This result suggests that CDDP-1 could have a functional relationship to retinoic acid signaling. A weak homology was observed between the amino acid sequences of CDDP-1 and SMRT (Silencing Mediator of Retinoid and Thyroid receptor; Chen and Evans, Nature 377: 454–457 (1995)). Transient assays with a retinoic acid response element ($\beta RE_2$)-dependent promoter-reporter failed to find any enhancement of promoter activity by CDDP-1 (data not shown) suggesting that CDDP-1 has no direct involvement in retinoic acid-dependent signaling.

Figure 2A:
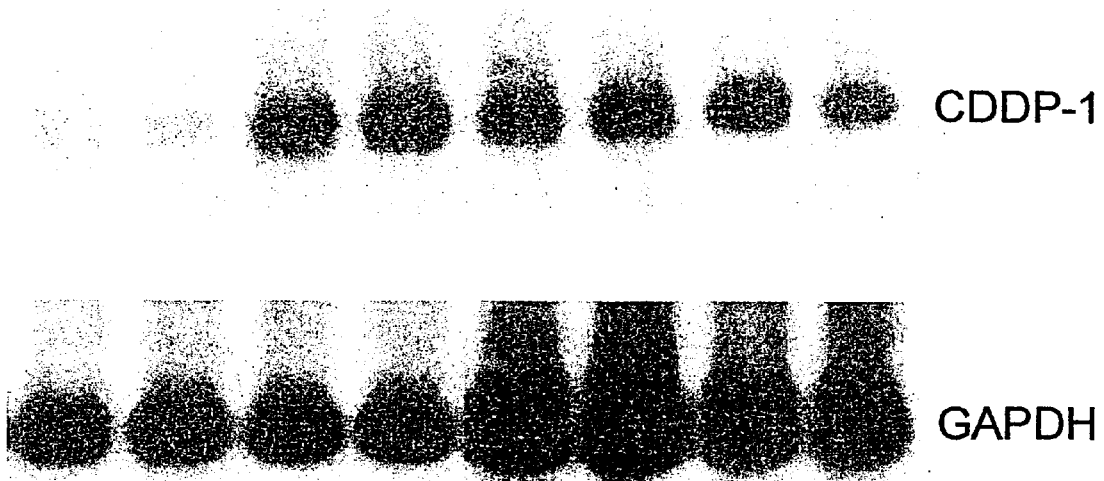
FIG. 2A shows a Northern blot confirming that the gene represented by the 230 bp CDDP-1 cDNA was expressed at a higher level in C/EBPβ-expressing cells (β1 and β2) than in controls, C1 and C2. The blot also shows that CDDP-1 is induced by C/EBPα (α1 (1 and α2), and C/EBPδ(δ1 and δ2) expression as well.
Figure 2B:
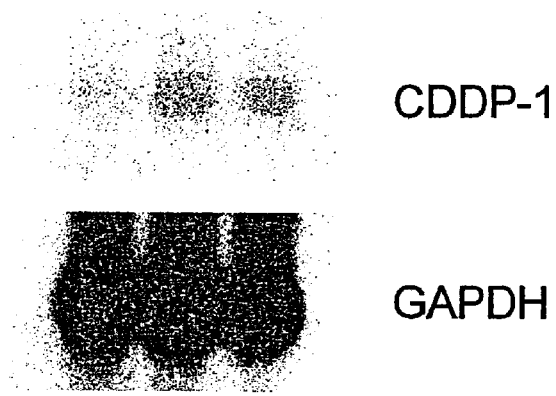
FIG. 2B shows a Northern blot confirming that the gene represented by the 230 bp CDDP-1 cDNA was expressed at a higher level in and C/EBPε (ε1 and β2)-expressing cells.

C/EBPα-deficient mice are completely lacking in neutrophils and eosinophils (Zhang et al., Proc. Natl. Acad. Sci. USA 94: 569 (1997)), while C/EBPα-deficient mice lack functional neutrophils and eosinophils (Yamanaka et al., Proc. Natl. Acad. Sci. USA 94: 13187–13192 (1997)). The G-CSF and the IL-6 receptors have been proposed as critical agents for neutrophilic differentiation. Transcription of the genes encoding G-CSF and IL-6 are regulated by C/EBPα. However, targeted-gene disruption experiments have shown that mice lacking the G-CSF and IL-6 receptors are still capable of producing mature neutrophils, albeit in reduced numbers (Zhang et al., J. Exp. Med. 188: 1173–1184 (1998)). The gene targets of C/EBPα and C/EBPε, which are responsible for the defects observed in animals that fail to express these transcription factors, have not been completely identified. Representational difference analysis, which was applied to the RNAs from fetal livers of wild-type and PU.1 or C/EBPα "knockout" mice, identified eight novel genes that are regulated during myeloid differentiation (Iwama et al., Nuc. Acids Res. 26: 3034–3043 (1998)). The function of these eight genes is unknown. The ability of CDDP-1 to promote differentiation of MPRO cells suggested that CDDP-1 could be a critical gene in the differentiation of neutrophils, which is regulated by C/EBPα and C/EBPε. Though CDDP-1 was originally isolated from cells through overexpression of C/EBPβ, subsequent experiments have shown that CDDP-1 expression was also upregulated by overexpression of C/EBPα, C/EBPδ, and C/EBPε (FIG. 2).

Analysis of the nucleic acid sequence upstream of the CDDP-1 translational start codon identified several potential C/EBP binding sites (FIG. 4). This suggests that CDDP-1 expression is directly regulated by C/EBPs.

Unexpectedly, the overexpression of CDDP-1 in MPRO cells yielded both neutrophilic and monocytic differentiation (FIG. 13). This unexpected result appears to be at odds with the reduced CDDP-1 expression that was observed upon monocytic differentiation of HL-60 cells (FIG. 11). However, the initial elevation of CDDP-1 expression prior to myeloperoxidase expression that was observed in 32D clone 3 cells could have reflected an early role for CDDP-1, which was prior to subsequent commitment to either the neutrophil or monocyte/macrophage pathway. The overexpression of CDDP-1 in a cell line with stem cell properties, such as EML-C1, will help to resolve this issue. For instance, CDDP-1-driven differentiation toward both pathways would strengthen the case for that CDDP-1 has a role in both neutrophil and monocyte/macrophage differentiation. The eventual production of CDDP-1-deficient mice can also help to resolve this issue by determining whether one or both differentiation pathways are affected in such animals. The modulation of CDDP-1 expression in both erythroid (FIGS. 18 and 19) and mast cell (FIG. 20) differentiation, as well as the observation of a uniquely sized RNA species in transformed pre-B cells (FIG. 21) suggests that CDDP-1 has a role in the differentiation of these other cells as well.

Since overexpression of CDDP-1 in MPRO promyelocytes promotes differentiation of the MPRO promyelocytes, inducing overexpression of CDDP-1 in malignant myeloid cells such as those associated with myeloid leukemia or lymphoma could promote the differentiation of the myeloid leukemia cells. This could would abrogate proliferation of the cells thereby rendering the cells non-malignant. Thus, either delivery of a vector that over expresses the CDDP-1 gene to malignant myeloid cells or treatment of malignant myeloid cells with agents that might induce CDDP-1 expression or overexpression could be an effective treatment for myeloid leukemias. In the cell lines that have been studied, treatment of the cell lines with retinoic acid appeared to induce CDDP-1 expression either directly or as the result of some unidentified downstream event. Retinoic acid has been a successful chemotherapeutic agent for some myeloid leukemias. Therefore, further inducing overexpression of CDDP-1 in myeloid leukemia cells could be expected to potentiate the action of retinoic acid, which would promote differentiation of the leukemic cells. Consistent with that expectation, overexpression of CDDP-1 in MPRO promyelocytes accelerated the rate of retinoic acid-induced differentiation in these cells.

Therefore, in one embodiment of the present invention, CDDP-1 can be used as an indicator in diagnostic assays wherein detection of CDDP-1 expression in a given leukemia or other malignant cell before and after treatment with particular chemical agents would provide a rational means for choosing appropriate chemotherapeutic agents for treating particular leukemias and other malignancies. Correlations between cell type, stage of differentiation, and susceptibility to chemotherapeutic agents would provide the basis for such use.

Such assays can be immunologically-based assays that use antibodies against CDDP-1 to detect CDDP-1 in cell protein extracts made from cells that have been treated with particular chemical agents. The immunologically-based assays can have a ELISA, radio-immunoprecipitation assay (RIA), or Western blot format. Such immunological methods are well known in the art. Alternatively, the assays can be nucleic acid-based and include assays such as Northern blotting to detect and quantify RNAs encoding CDDP-1 in cells treated with particular chemical agents, and RT-PCR (reverse transcription-polymerase chain reaction)-based assays such as conventional RT-PCR and RT-PCR based upon TAQMAN energy donor and acceptor technology (Applied Biosystems Division, Perkin-Elmer, Foster City, Calif.). RT-PCR assays are particularly useful for quantifying the amount of RNA encoding CDDP-1 that is expressed. When using RT-PCR, it is preferable that one PCR primer of the PCR primer pair be complimentary to a sequence in a first exon and the other PCR primer of the primer pair be complimentary to a sequence from an exon adjacent to the first exon. Because genomic DNA encoding CDDP-1 has an intron between the adjacent exons, the above primer pair minimizes inadvertently detecting genomic DNA or unprocessed pre-mRNA encoding CDDP-1.

Either the immunologically-based or the nucleic acid-based assay can be used to identify synergistic agents, which when provided to nondifferentiated cells amplify the effective concentration or activity of CDDP-1. Synergistic agents include, but are not limited to, polypeptides or non-polypeptide factors that facilitate the binding of CDDP-1 to its target, stabilize either CDDP-1 or its mRNA from degradation or inactivity, or act to increase the rate of transcription or translation of CDDP-1. The above assays can be conveniently provided as a kit, which provides either antibodies against CDDP-1 or DNA probes or PCR primers complimentary to the nucleic acid encoding CDDP-1. The kit can further include controls for monitoring the specificity and sensitivity of the assays. Preferably, the kit further provides a means for detecting antibody-CDDP-1 complexes or probe-CDDP-1 RNA complexes. Detection means, which include, but are not limited to, radioactive labels, enzymatic labels such as horseradish peroxidase and alkaline phosphatase, and fluorescence labels, are well known in the art.

Thus, the above assays and kits can evaluate the capacity of a chemical agent to potentiate or complement the effect of CDDP-1 on cell differentiation. Such chemical agents are functional analogs of CDDP-1 and can be of two types: classical analogs and mimetic analogs. A classical analog of CDDP-1 is a molecule that has a biological activity similar to CDDP-1 and is chemically related to CDDP-1. For example, a non-naturally occurring mutant polypeptide having CDDP-1 activity would be a classical analog and a mutated nucleic acid encoding CDDP-1 is a classical analog of the naturally occurring CDDP-1 gene sequence. On the other hand, a mimetic analog of CDDP-1, which has an activity similar to the activity of CDDP-1, is chemically unrelated to CDDP-1. An organic molecule whose structure mimics the active site of CDDP-1 would be an example of a mimetic analog of CDDP-1. Mimetic analogs are particularly desirable because in many cases, the analogs are relatively stable and can readily cross cellular membranes whereas polypeptides are subject to degradation by proteases and do not easily pass through cellular membranes. Therefore, a CDDP-1 mimetic analog can be used to induce undifferentiated myeloid cells to differentiate into neutrophils and/or monocytes/macrophages by exposing the undifferentiated cells to a solution containing the mimetic analog. For example, a solution comprising a CDDP-1 mimetic analog can be administered to undifferentiated cells or cell mass in a patient using intravenous methods.

Functional analogs of CDDP-1 can be either a proteinaceous compound or preferably a non-proteinaceous compound, provided that the analog mimics the function of either the entire CDDP-1 molecule or relevant portions of the CDDP-1 molecule. Preferably, the classical analogs include polypeptides whose sequences comprise the active portions of the CDDP-1 molecule, either a catalytic site or one or more binding sites, or nucleic acid fragments that encode the active portion or portions of the CDDP-1 (catalytic or binding sites). The preferred mimetics include polypeptides that are not polypeptide fragments of CDDP-1 or organic compounds and which have the ability to act like CDDP-1 in undifferentiated cells.

Classical analogs can be obtained using mutagenic methods such as random or site-directed mutagenesis. Both mutagenic methods involve altering the nucleic acid encoding CDDP-1 to produce mutant CDDP-1 molecules that have enhanced CDDP-1 characteristics. Random mutagenesis requires prior information about the gene sequence to be mutated. This can be advantageous in that it assesses the desirability of a particular mutation on the basis of its function, and does not require an understanding of how or why the resultant mutant protein has adopted a particular conformation. Alternatively, where a particular sequence mutation is desired, methods of site-directed mutagenesis can be used or the particular sequence mutation can be programmed into an automated DNA synthesizer to produce the mutated nucleic acid. Such site-directed mutagenesis methods can be used to alter only those particular amino acids believed to be important. Analysis of the above mutants can be facilitated through the use of phage display screening systems.

Mimetic analogs of CDDP-1 can be obtained using the principles of conventional or rational drug design. In accordance with the methods of rational drug design, the mimetic analog of CDDP-1 is designed to share one or more attributes of the three-dimensional conformation of the CDDP-1 molecule. Thus, the mimetic analog can be designed to possess chemical groups that are oriented in a way sufficient to cause ionic, hydrophobic, or van der Waals interactions that are similar to those of CDDP-1. Identifying mimetic analogs can be performed using a computer system that can form a three-dimensional structure of CDDP-1 and enable organic structures to be superimposed. In accordance with conventional drug design, mimetic molecules are obtained by randomly screening molecules that have an attribute in common with CDDP-1, or a molecule that interacts with CDDP-1. Such screening tests quantitatively measure the capacity of competition or cooperativity between the CDDP-1 and the CDDP-1 mimetic analog.

The CDDP-1 of the present invention also provides a means for treating malignant cancers caused by proliferation of undifferentiated cells such as myeloid leukemia cells whose onset or maintenance is characterized by and dependent upon a decreased cellular expression of CDDP-1. In particular, the invention provides a means for inducing differentiation of myeloid leukemia cells, which thereby inhibits the continued proliferation of the myeloid leukemic cells. As used herein, the term "inhibition" means a process wherein the extent or rate of proliferation of the treated cells is abrogated or diminished relative to untreated undifferentiated cells.

Treatments that inhibit proliferation of undifferentiated cells such as cancerous, malignant, or undifferentiated cells can be accomplished by either initiating CDDP-1 expression or increasing CDDP-1 expression in the cells relative to CDDP-1 expression in the untreated cells. In one embodiment, gene therapy methods are used wherein DNA encoding either a functional CDDP-1 gene, variants of the CDDP-1 gene, or other genes that influence the activity or expression of the CDDP-1 gene are introduced into vectors that are capable of transfecting undifferentiated cells such as myeloid leukemia cells. Most preferably, virus vectors such as retrovirus, adeno-associated virus, or other suitable virus vectors are used to introduce the DNA encoding CDDP-1 into the cells. Furthermore, it is preferable that the CDDP-1 be transcribed from a promoter that is transcribed only, or preferentially, in the undifferentiated cancerous or malignant cells. Promoters that are preferentially transcribed in cancerous cells are those that control transcription of tumor specific antigens and include, but are not limited to, alpha-fetoprotein, carcinoembryonic antigen, amylase, and gamma-glutamyl transferase. Gene therapy can be provided as a therapeutic treatment to induce differentiation of the undifferentiated cells or to provide a prophylactic treatment to those individuals who have an inherited genetic mutation that results in impaired expression of CDDP-1.

The present invention also provides a method for altering the nature or control of cell differentiation in undifferentiated cells such as undifferentiated myeloid cells. The present invention permits the manipulation of the CDDP-1 gene to produce mutants, which can be used to identify CDDP-1 variants or mutants, antagonists, and synergistic agents that would be suitable for inducing undifferentiated cells to differentiate. For example, the invention enables mutations to be created in the CDDP-1 gene or promoter, which result in increased CDDP-1 expression.

The CDDP-1 polypeptide, nucleic acids encoding CDDP-1, and CDDP-1 "knockout" transgenic animals are particularly suitable for use in determining the physiological significance of CDDP-1, particularly its role in cell differentiation. The "knockout" animals are particularly useful for determining how CDDP-1 promotes or induces differentiation of particular cell types in the animal including diseases caused by various proliferating undifferentiated cell populations. Both transgenic animals that are heterozygous "knockouts" (deficient for one of the CDDP-1 alleles) and homozygous "knockouts" (deficient for both of the CDDP-1 alleles) are useful. Preferably, the transgenic animals are transgenic mice which are either heterozygous deficient or homozygous deficient for the CDDP-1 chromosomal alleles. Methods for making "knockout" mice are well known in the art. Results from analyses with these transgenic animals can lead to development of effective treatments and therapies for leukemias and other diseases caused by proliferation of undifferentiated cells.

The following examples are intended to promote a further understanding of the present invention.

EXAMPLE 1

The following discloses the isolation and characterization of CDDP-1.

Materials and Methods

Cell Lines and Cell Culture Methods. 32D clone 3 murine myeloblasts (Valteri et al., J. Immunol. 138: 3829–3835 (1987)) were grown in Iscove's modified Dulbecco's medium (IMDM) supplemented with 20% fetal calf serum (FCS) and 10% WEHI-3 conditioned medium as a source of interleukin-3. For induction of granulocyte differentiation, cells were washed twice with phosphate-buffered saline and placed in IMDM supplemented with 20% FCS supplemented with 5 ηg/ml G-CSF (R & D Systems, Minneapolis, Minn. 55413).

WEHI-3 cells (obtained from the American Type Culture Collection (ATCC), 10801 University Boulevard, Manasas, Va. 20110, as ATCC TIB 68) were maintained in Roswell Park Memorial Institute (RPMI) 1640 medium supplemented with 5% FCS.

EML-C1 murine hematopoietic progenitor cells, a cell line created by immortalizing bone marrow cells with LRARα430SN, a retroviral vector encoding a truncated retinoic acid receptor (RAR) (Tsai et al., Genes & Dev. 8: 2831–2841 (1994)), were maintained in IMDM supplemented with 20% horse serum and 15% conditioned medium from BHK cells transfected with an expression vector for rat stem cell factor (BHK/MKL cells).

For induction of myelomonocytic differentiation, EML-C1 cells were transferred to IMDM supplemented with 20% horse serum, 15% BHK/MKL conditioned medium, 10% WEHI-3 conditioned medium, and 5 μM all-trans retinoic acid (ATRA). For induction of erythroid differentiation, EML-C1 cells were transferred to IMDM supplemented with 20% horse serum, 15% BHK/MKL conditioned medium, 0.5% WEHI-3 conditioned medium, and 8 units/ml human erythropoietin (R & D Systems). For induction of mast cell differentiation, EML-C1 cells were transferred to IMDM supplemented with 20% horse serum, 15% BHK/MKL conditioned medium, and 10% WEHI-3 conditioned medium.

MPRO murine promyelocytes were grown in Dulbecco's modified Eagle's medium (DMEM) supplemented with 10% heat-inactivated FCS and 10 ηg/ml murine granulocyte-macrophage colony-stimulating factor (R & D Systems). MPRO promyelocytes were derived by Tsai and Collins, Proc. Natl. Acad. Sci. USA 90: 7153–7157 (1993), from freshly harvested mouse bone marrow cells infected with LRARα430SN. For induction of granulocyte differentiation, ATRA was added to a final concentration of 20 μM.

HL-60 human promyelocyte leukemia cells (obtained from the ATCC as ATCC CCL 240), which had been isolated from the peripheral blood of a patient with acute promyelocytic leukemia and exhibits myc oncogene expression, were maintained in RPMI 1640 medium supplemented with 20% FCS. HL-60 cells were treated with either 10 μM ATRA or 100 ηM phorbol myristate acetate to induce granulocytic or monocytic differentiation, respectively.

BB88 Friend erythroleukemia cells (obtained from the ATCC as ATCC TIB 55), which were derived from a leukemia induced by B-tropic Friend murine leukemia virus, were grown in RPMI 1640 supplemented with 10% heat-inactivated FCS and 2-mercaptoethanol. For induction of erythroid differentiation and hemoglobin synthesis, dimethyl sulfoxide was added to a final concentration of 15% (v/v).

U937 human histiocytic lymphoma cells (obtained from the ATCC as ATCC CRL 1593), which were derived from malignant cells obtained from the pleural effusion of a patient with histiocytic lymphoma, were grown in RPMI 1640 supplemented with 10% FCS. U937 cells were treated with either 10 μM ATRA or 100 ηM phorbol myristate acetate to induce granulocytic or monocytic differentiation, respectively.

293T cells (Pear et al., Proc. Natl. Acad. Sci. USA 90: 8392–8396 (1993)) and CV-1 cells (obtained from the ATCC as ATCC CCL 70) were grown in DMEM supplemented with 10% FCS.

All cell cultures were grown at 37° C. in a 5% $CO_2$ atmosphere.

Differential Display RT-PCR, cDNA Cloning and Sequencing. Differential display RT-PCR was performed with the Delta RNA Fingerprinting Kit (available from Clontech Laboratories, Palo Alto, Calif.) according to the manufacturer's instructions. The full length cDNA encoding CDDP-1 was isolated from a λgt11 human bone marrow cDNA library (obtained from Clontech). The library was screened according to the manufacturer's protocol using the 230 bp CDDP-1 differential display product, as well as a probe generated by 5' rapid amplification of cDNA ends, as probes. Two rounds of screening were performed to eventually isolate a 2.3 kb cDNA encoding CDDP-1. Automated dye terminator sequencing was performed by the Michigan State University DNA Sequencing Facility, Michigan State University, East Lansing, Mich. 48824.

RNA Isolation and Analysis. Total RNA was isolated using TRIZOL reagent (available from Life Technologies, Rockville, Md.) according to the manufacturer's instructions. RNAs were electrophoresed through 1% agarose/formaldehyde denaturing gels. For Northern blots, the resolved RNAs were transferred to membranes, which were hybridized and washed to a stringency of 0.1×SSPE at 65° C. Hybridization probes were prepared with a random priming kit (Life Technologies) and radiolabled by incorporating 5'-[$\alpha$-$^{32}$P]dATP (3000 Ci/mmol; DuPont-New England Nuclear, Boston, Mass.). The C/EBP$\alpha$ and C/EBP$\beta$ probes were rat genomic DNA fragments derived from the pSV(X)C/EBP$\alpha$ and pSV(X)C/EBP$\beta$ expression vectors (Hu et al., J. Immunol. 160: 2334–2342 (1998)). The C/EBP$\delta$ probe was a murine genomic DNA fragment derived from the pSV(X)C/EBP$\delta$ expression vector (Hu et al., ibid.). The C/EBP$\epsilon$ probe was a rat genomic DNA fragment derived from the pSV(X)C/EBP$\epsilon$p34 expression vector (Williams et al., J. Biol. Chem. 273: 13493–13501 (1998)). The myeloperoxidase probe was a 0.8 kb PstI DNA fragment derived from a 2.73 kb murine cDNA (provided by G. Rovera, the Wistar Institute, Philadelphia, Pa). The fms probe was a 2.7 kb ClaI/BamHI DNA fragment of the McDonough strain of feline sarcoma virus (Donner et al., J. Virol. 41: 489–500 (1982)). The lysozyme probe was a 1.0 kb human cDNA (Peters et al., Eur. J. Biochem. 182: 507–516 (1989)). The cathepsin G probe was a 0.5 kb murine cDNA cloned using the differential display RT-PCR process described herein. The glyceraldehyde-3-phosphate dehydrogenase probe was a 1.3 kb rat cDNA (Fort et al., Nuc. Acids Res. 13: 1431–1442 (1985)).

Expression Vectors. Plasmid pSV(X)C/EBP$\beta$ expresses C/EBP$\beta$ from the gene encoding C/EBP$\beta$ operably linked to the Moloney murine leukemia virus promoter. Construction of pSV(X)C/EBP$\beta$ from the parent vector, pSV(X)Neo, is described in Bretz et al., Proc. Natl. Acad. Sci. USA 91: 7306–7310 (1994) and Hu et al., J. Immunol. 160: 2334–2342 (1998). Plasmid pBABE-CDDP-1, which expresses CDDP-1 from the cDNA encoding CDDP-1 operably linked to the Moloney murine leukemia virus promoter, was constructed by inserting the CDDP-1 cDNA into the BamHI site of the murine retroviral vector, pBABE-Puro (Morgenstern and Land, Nuc. Acids Res. 18: 3587–3596 (1990)). Plasmid pMTD-CDDP-1 was constructed by inserting the CDDP-1 cDNA into the BglII site of PMTD (Sompayrac and Danna, Virol. 200: 849–853 (1994)), which placed CDDP-1 expression under the control of a modified metallothionein promoter. Plasmid pMEX-CDDP-1 was constructed by inserting the CDDP-1 cDNA into the EcoRI site of pMEX (Williams, et al., Genes & Dev. 5: 1553–1567 (1991)), which placed CDDP-1 expression under the control of the Moloney murine sarcoma virus promoter. Plasmid $\beta$-RE2-Luc (provided by Ron Evans, The Salk Institute, San Diego, Calif.) contains two copies of the retinoic acid response elements and the luciferase gene. Plasmid pCMV-RAR$\alpha$ (provided by David Talmage, Columbia University, New York, N.Y.) expresses the gene encoding the human retinoic acid receptor $\alpha$ operably linked to the cytomegalovirus promoter. The SV40 early promoter-reporter plasmid, p$\beta$gal-Control, which was used as a control for transient transfections, is commercially available from Clontech. Plasmid p$\beta$gal-Control has the SV40 early promoter and enhancer sequences cloned upstream and downstream, respectively, of the lacZ gene.

Retroviral infections. In order to prepare retrovirus stocks derived from pSV(X)Neo, pSV(X)C/EBP$\beta$, pBABE-Puro, and pBABE-CDDP-1, 6 cm plates of about 70% confluent 293T cells were co-transfected with 3 $\mu$g of pMOV-$\psi$ (a retrovirus packaging construct described in Mann et al., Cell 33: 153–159 (1983)), 3 $\mu$g pBABE-CDDP-1, and DMRIE-C reagent (available from Life Technologies) according to the manufacturer's directions. Sixty hours post-transfection, viral supernatants were collected by centrifugation at 1000 rpm for 5 minutes and filtered through 0.4 $\mu$m filters. Then, about 2×10$^6$ cells in normal growth medium were mixed with an equal volume of viral stock and 8 $\mu$g/ml polybrene (Sigma Chemicals, Inc., St. Louis, Mo.). The mixture was incubated at 37° C. for 3 hours. Infected cells were recovered by centrifugation and resuspended into appropriate growth medium. Twenty-four hours after infection, the cell cultures were split 1:4 and puromycin was added into the media to a final concentration of 1 $\mu$g/ml for a period of 1 to 2 weeks.

Transient Transfections. Transient transfections of CV-1 cells were performed using DMRIE-C reagent following the manufacturer's instructions. $\beta$-RE2-Luc and pCMV-RAR$\alpha$ were co-transfected in the presence or absence of pMEX-CDDP-1 as follows. Total DNA was made up to 3 $\mu$g for each transfection with pMEX. Transfected cells were either treated or untreated with 10 $\mu$M ATRA. An SV40 early promoter-reporter (p$\beta$gal-Control) was used as a control to monitor transfection efficiency. Forty-eight hours post-transfection, the cells were lysed and analyzed for luciferase activity using the Luciferase Reporter Gene Assay Kit (Roche Molecular Biochemicals, Indianapolis, Ind.) and for $\beta$-galactosidase activity using the Luminescent $\beta$-Galactosidase Genetic Reporter System II (Clontech).

Western blotting. Whole cell protein extracts were prepared using TRIZOL reagent (Life Technologies) following the manufacturer's instructions. To prepare cytoplasmic and nuclear fractions, about 5×10$^6$ cells were washed in phosphate buffered saline and lysed in 200 $\mu$l buffer A (15 mM KCl, 10 mM HEPES [pH 7.5], 2 mM MgCl$_2$, 0.1 mM EDTA, 1 mM dithiothreitol, 0.1% (v/v) NP-40, 0.5 mM phenylmethylsulfonyl fluoride (PMSF), 2.5 $\mu$g/nl leupeptin, 5 $\mu$g/ml antipain, and 5 $\mu$g/ml aprotin) for 10 minutes on ice. The nuclei were pelleted by centrifugation at 14,000×g for 20 seconds. The supernatant was the cytoplasmic fraction. Proteins were extracted from the nuclei at 4° C. with vigorous vortexing in buffer C (420 mM NaCl, 20 mM HEPES [pH 7.9], 0.2 mM EDTA, 25% (v/v) glycerol, 1 mM dithiothreitol, 0.5 mM PMSF, 2.5 $\mu$g/nl leupeptin, 5 $\mu$g/ml antipain, and 5 $\mu$g/ml aprotinin). Nuclear debris was removed by centrifugation at 14,000×g for 15 minutes at 4° C. to produce the nuclear fraction. Aliquots from the nuclear and cytoplasmic fractions were resolved by sodium dodecyl sulfate (SDS)-12% polyacrylamide gel electrophoresis. After electrophoresis, the resolved proteins were transferred to a PROTRAN membrane (Schleicher and Schuell, Keene, N.H.). Western blotting was performed using antiserum against either CDDP-1, cytoplasmic dehydrogenase, or nuclear SM protein using procedures well known in the art. Afterwards, the protein-antibody complexes were visualized using the Enhanced Chemiluminescence Kit (Amersham Pharmacia Biotech Inc., Piscataway, N.J.).

Antisera. A 540 bp BamHI DNA fragment encoding CDDP-1 was subcloned into pGEX-2 (Amersham Pharmacia Biotech) to produce pGEX-CDDP-1, which produces CDDP-1 as a GST-CDDP-1 fusion protein. pGEX-CDDP-1 was transformed into E. coli and the transformed E. coli grown in bacterial cultures to produce the GST-CDDP-1 fusion protein. The bacteria were harvested and lysed to provide a bacterial extract. The GST-CDDP-1 fusion protein was purified from the bacterial extract by glutathione SEPHAROSE 4 B column chromatography (Amersham Pharmacia Biotech). The purified GST-CDDP-1 fusion protein was used to immunize rabbits according to methods well known in the art to produce antiserum against CDDP-1. Both the immunizations and serum preparations were performed by Alpha Diagnostic International, San Antonio, Tex. Antiserum against cytoplasmic lactate dehydrogenase and nuclear SM protein were obtained from Ronald Patterson (Michigan State University, East Lansing, Mich.).

Cell Staining. MPRO transductant cells were cytocentrifuged onto glass microscope slides and stained in Wright-Giemsa Stain (Sigma Chemicals, Inc.) according to the manufacturer's instructions.

Results

Identification and Sequence Analysis of CDDP-1. DNA encoding CDDP-1 was identified from a series of differential display RT-PCR experiments by comparing RT-PCR products from 32D clone 3 myeloblasts infected with a retroviral vector expressing C/EBPβ to RT-PCR products from 32D clone 3 myeloblasts infected with an "empty" control vector. Sixty-four sets of RT-PCR primers were used to identify 27 differential display cDNA products that potentially represented both gains and losses of expression of particular RNAs upon C/EBPβ expression. Northern blots comparing RNA from C/EBPβ transformed cells to RNA from the original cell lines used to generate the differential display confirmed that four of these products were differentially expressed as a result of C/EBPβ expression. Sequencing the four differentially expressed cDNA products showed that two of these cDNA products were derived from RNAs containing retroviral sequences (most murine cell lines contain multiple copies of endogenous retroviruses which have C/EBP binding sites in their long terminal repeats). A third cDNA product represented an RNA that encoded a portion of cathepsin G, a neutral serine protease found in the primary granules of neutrophils. However, the sequence for the fourth cDNA product, which produced the 230 bp cDNA shown in FIG. 1, represented an unknown RNA. As shown in FIG. 2, Northern blots of RNA isolated from 32D clone 3 cells transduced for C/EBPβ, C/EBPα, or C/EBPδ expression and probed with the 230 bp cDNA verified that this cDNA product represented RNA that was being overexpressed in the C/EBP transduced 32D clone 3 cells. This indicated that the gene encoding the unknown RNA was regulated by C/EBP. The product encoded by the unknown RNA was designated C/EBP Differential Display Product 1 (CDDP-1).

Comparing the 230 bp cDNA sequence to the nucleic acid sequences in GenBank showed that the 230 bp cDNA sequence encoded a novel gene product that had not been previously reported. However, several highly homologous EST (expressed sequence tag) clones from mouse, rat and human were identified but these EST clones encoded polypeptides that were of unknown function. Because the human EST clones contained a highly homologous sequence, it was reasoned that a commercially available λgt11 human bone marrow cDNA library screened with the 230 bp cDNA as a probe would enable a full-length cDNA clone encoding CDDP-1 to be identified and isolated. A cDNA clone that hybridized to the 230 bp cDNA probe was identified and sequenced. The nucleotide sequence of the cDNA clone is shown in FIG. 3 and is set forth in SEQ ID NO:1. By translating the clone in all three reading frames, it was discovered that the clone contained an open reading frame that encoded a novel 453 amino acid polypeptide, designated CDDP-1. The amino acid sequence of CDDP-1 is shown in FIG. 3 and is set forth in SEQ ID NO:2. The CDDP-1 has a predicted molecular weight of about 45 kD.

National Center for Biotechnology Information GenBank BLAST analyses of both the amino acid sequence of the CDDP-1 polypeptide and the nucleic acid sequence encoding CDDP-1 showed that neither the CDDP-1 polypeptide nor its cDNA had any significant identity to any known protein or nucleic acid listed in GenBank. Analyses for protein motifs, which might provide a clue as to the mechanistic function of CDDP-1, showed only that CDDP-1 contained several potential protein kinase c and casein kinase 2 sites, and a potential N-glycosylation site. Interestingly, a protein BLAST search identified a protein of unknown function, which was related to CDDP-1 (GenBank Accession No. AAD50514) and was supported by several human ESTs with 43% identity to the amino acid sequence of CDDP-1. This suggested that CDDP-1 may be a member of a larger family of as yet uncharacterized proteins.

A sequence tag site (STS-W37771) identical to CDDP-1 was found to be located on human chromosome 17q21-q22 of the GB4 radiation hybrid map, a region with a number of mapped chromosomal abnormalities observed in leukemias. While some chromosomal abnormalities in this region involve genes encoding the retinoic acid receptor α, hepatic leukemia factor, and AF17, other genes in this region have not been identified. The CDDP-1 cDNA sequence was identical to portions of the unordered sequences reported to GenBank as "unfinished High Throughput Genomic Sequences" (Accession No. AC015795). However, an open reading frame within the STS corresponding to CDDP-1 had not been identified. The failure to identify the CDDP-1 open reading frame in the unordered sequences was because CDDP-1, like most eukaryote genes, consists of exons and introns, i.e., short (about 300 bp) coding regions (exons) wherein each exon is separated from other exons by intervening sequences (introns) that can range in size from about 100 bp to over 30,000 bp. In general, a eukaryote gene contains a plurality of contiguous exons and introns which are transcribed in the nucleus into a pre-mRNA containing the contiguous exons and introns. During RNA processing the introns are spliced from the pre-mRNA and the exons flanking each intron are ligated together to produce an mRNA comprising the ligated exons. Because the nucleotide sequence at exon/intron boundaries is highly degenerate, identification of open reading frames or genes within eukaryote genomic DNA is nearly impossible. Since a cDNA is a copy of a mRNA that has had the introns removed, the only practical way to identify an open reading frame or gene in genomic DNA is to first know the sequence for an open reading frame or gene encoded by a cDNA and use the cDNA sequence to identify the exons in the genomic DNA. Therefore, as a practical matter, it would not have been possible to identify the chromosomal gene encoding CDDP-1 without access to the cDNA encoding CDDP-1. However, by comparing the unordered sequences from human chromosome 17 to the CDDP-1 cDNA sequence the genomic gene encoding CDDP-1 was discovered. The comparison showed that the CDDP-1 gene is organized into 8 exons corresponding to cDNA nucleotides 16–226, 227–393, 394–491, 492–602, 603–738, 739–939, 940–1093, and 1094–2314. An examination of untranslated sequences upstream of the first exon (SEQ ID NO.3) found several potential C/EBP binding sites, which is consistent with the upregulation of CDDP-1 by overexpression of particular C/EBP isoforms (FIG. 4).

CDDP-1 is Most Highly Expressed in Fetal Liver and Adult Bone Marrow. Hybridization of the CDDP-1 cDNA to an RNA dot blot of mRNA isolated from particular human tissues using the RNA Master Blot (available from Clontech) found mRNA encoding CDDP-1 to be expressed most highly in fetal liver and adult bone marrow, which was 4.2-fold and 3.0-fold, respectively, of the level seen in peripheral leukocytes. This result, shown in FIG. 5, is what would be expected for a gene that had a function in hematopoiesis.

Figure 6:
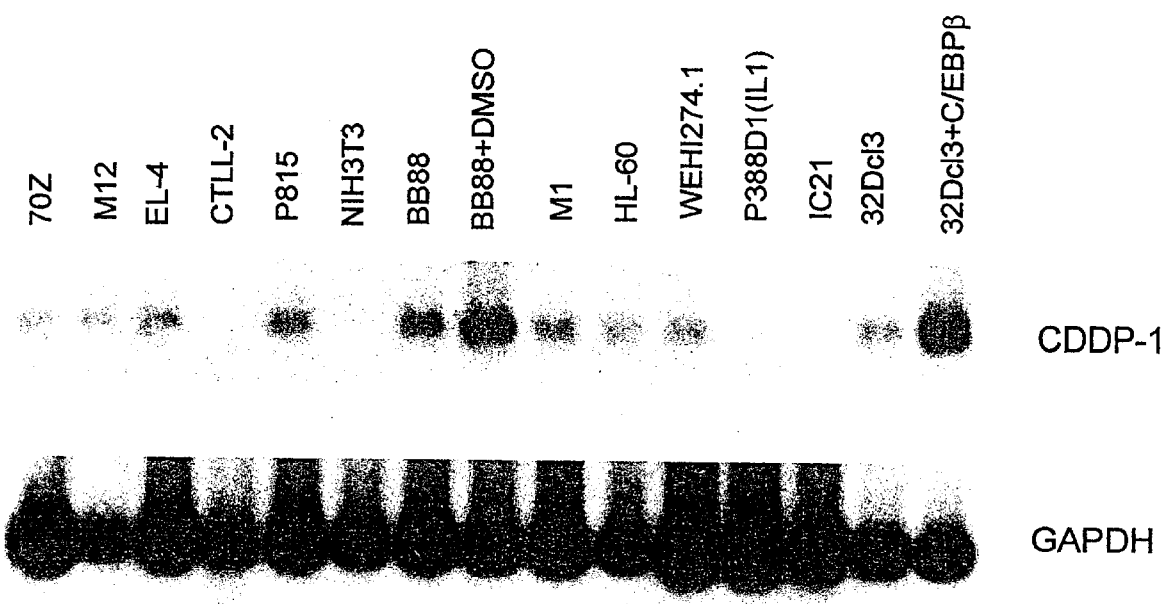
FIG. 6 shows a Northern blot of RNAs from a variety of hematopoietic cells probed with the CDDP-1 cDNA.

In FIG. 6, a Northern blot of a diverse panel of RNA isolated from hematopoietic cell lines showed that in addition to expression of CDDP-1 encoding mRNA in myeloblast cell lines 32D clone 3 (M1 and HL60), CDDP-1 encoding mRNA was expressed in the monocytic cell line (WEHI 274.1). However, CDDP-1 mRNA expression was lacking in mature macrophage cell lines (IC21 and P388D1 (IL-1)). CDDP-1 mRNA expression was also observed in a B cell line (M12), a pre-B cell line (70Z/3), a CD4+ pre-T cell line (EL4), a mastocytoma (P815), and an erythroblast cell line (BB88). In the case of BB88, CDDP-1 mRNA expression was increased upon DMSO-induced differentiation. CDDP-1 mRNA expression was neither observed in a CD8+ T cell line (CTLL-2) nor in NIH3T3 cells.

Figure 7:
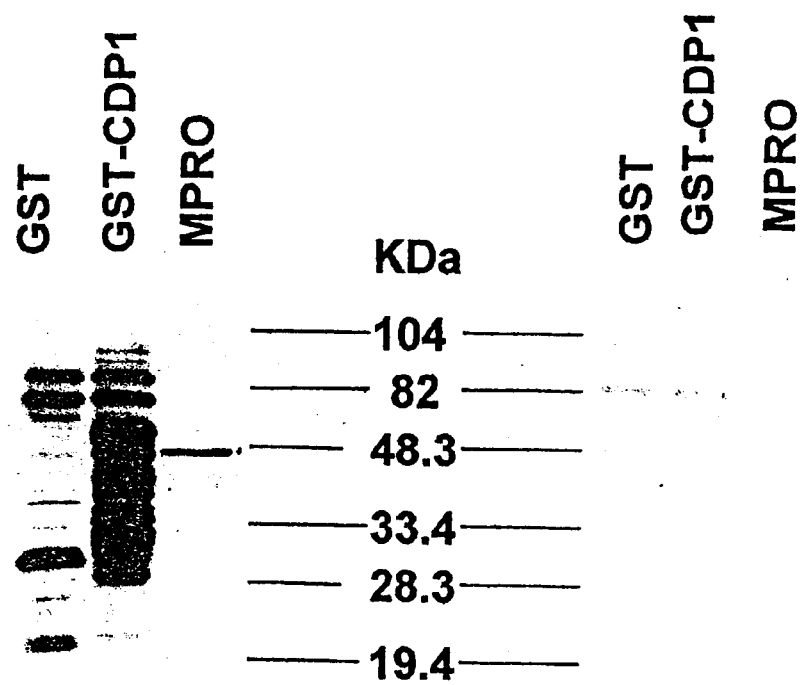
FIG. 7 shows a Western blot comparing CDDP-1 antiserum to pre-immune serum. The samples were a control bacterial lysate with GST protein (GST), a bacterial lysate containing the GST-CDDP-1 fusion protein (GST-CDDP-1), and a cellular lysate of MPRO cells.

CDDP-1 is Predominantly a Cytoplasmic Protein. An antibody specific for CDDP-1 was used to verify expression of CDDP-1, determine its localization within the cell, and to perform immunoprecipitations to detect proteins associated with CDDP-1. A GST-CDDP-1 fusion protein was prepared and used to immunize rabbits. Serum was prepared from the immunized rabbits and used to probe Western blots containing the GST-CDDP-1 fusion protein and a cell extract from MPRO cells separated by SDS gel electrophoresis. FIG. 7 shows that the anti-GST-CDDP-1 antiserum detected a 48 kD protein in the MPRO cell extract that was in close agreement with the calculated molecular weight of 45 kD for CDDP-1 predicted by the amino acid sequence in SEQ ID NO.2.

Figure 8A:
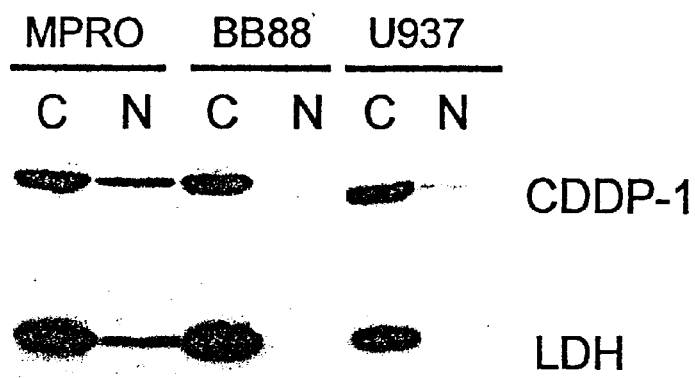
FIG. 8A shows a Western blot comparing the cytoplasmic (C) and nuclear (N) fractions from MPRO, BB88, and U937 cells. The blots were reacted with antiserum specific to CDDP-1, lactate dehydrogenase (LDH), SM, and retinoic acid receptor (RARα).
Figure 8B:
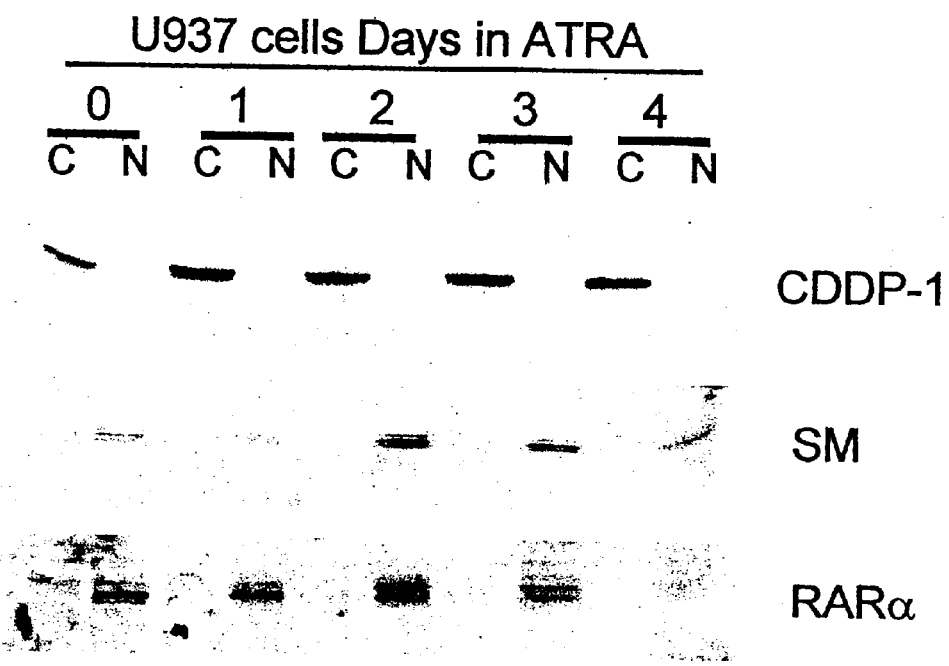
FIG. 8B shows a Western blot comparing the cytoplasmic (C) and nuclear (N) fractions of a time course of U937 neutrophilic differentiation induced by ATRA for four days. The blots were reacted with antiserum specific to CDDP-1, lactate dehydrogenase (LDH), SM, and retinoic acid receptor (RARα).

The anti-GST-CDDP-1 serum was also used to determine whether CDDP-1 was predominantly a nuclear protein or a cytoplasmic protein. Western blots containing nuclear and cytoplasmic extracts from MPRO, BB88, and U937 cells separated by SDS gel electrophoresis were probed with anti-GST-CDDP-1 antiserum. As a control, the Western blots were probed with anti-lactate dehydrogenase antiserum. Lactate dehydrogenase is an exclusively cytoplasmic protein. As shown in FIG. 8, CDDP-1 appears to be predominantly a cytoplasmic protein. The CDDP-1 that appears in the nuclear extracts is likely to be an artifact because in similar blots probed with anti-lactate dehydrogenase antiserum, a similar amount of lactate dehydrogenase was found in the nuclear extracts as well.

To examine whether the subcellular localization of CDDP-1 changes as cells differentiate, the U937 cells were treated with ATRA to induce neutrophilic differentiation. Both cytoplasmic and nuclear extracts were prepared over a time course of four days. Western blots of the extracts probed with anti-GST-CDDP-1 antiserum showed that the CDDP-1 protein could only be detected in the cytoplasmic fractions. As a control for nuclear protein, SM protein, which is a component of spiceosome, could only be found in the nuclear fractions. As an additional control, RARa, a transcription factor that appeared in both the cytoplasmic and nuclear fractions in untreated cells, translocated into the nucleus upon ATRA treatment. The above evidence strongly indicates that CDDP-1 is predominately a cytoplasmic protein. Immunofluorescent experiments using CDDP-1 specific-antiserum in MPRO promyelocytes showed that CDDP-1 existed mainly in the cytoplasm (data not shown).

Figure 9:
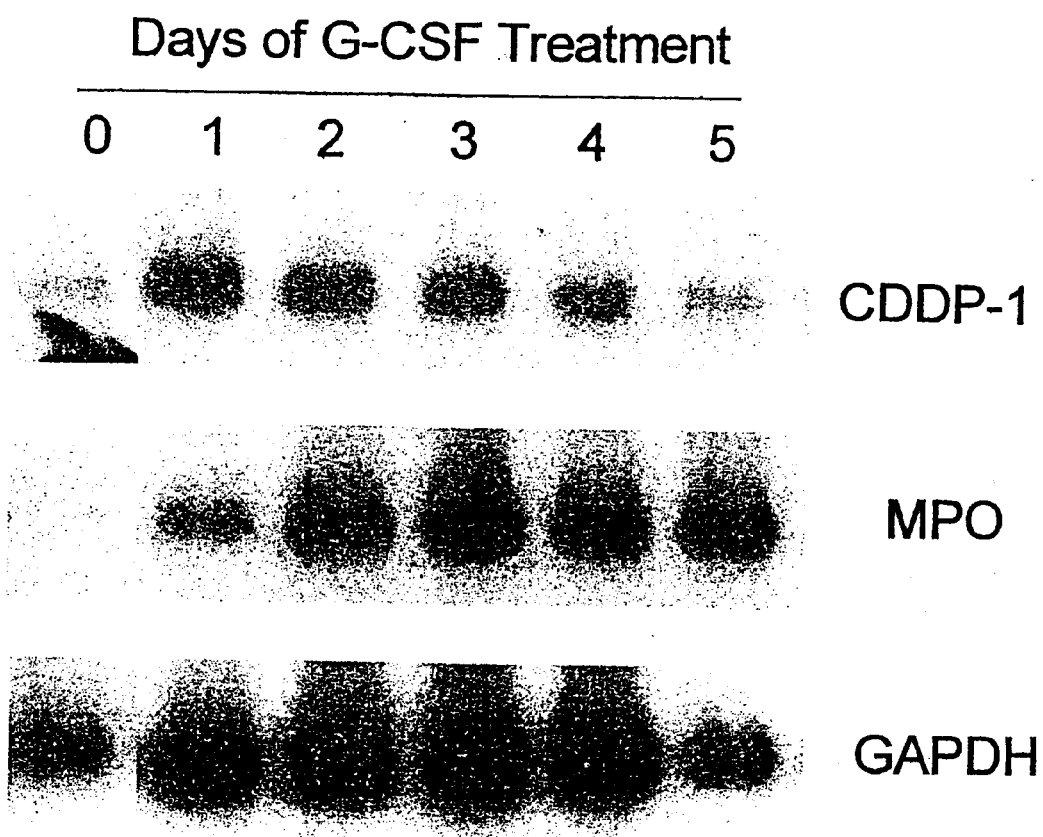
FIG. 9 shows a Northern blot of RNA isolated from a time course of G-CSF-induced differentiation of 32D clone 3 cells. The blot was successively hybridized with nucleic acid probes for CDDP-1, myeloperoxidase (MPO), and glyceraldehyde-3-phosphate dehydrogenase (GAPDH).

CDDP-1 mRNA is Upregulated During Neutrophilic Differentiation and Downregulated During Monocytic Differentiation. The necessity for C/EBPα expression in neutrophilic differentiation and by inference, the necessity for C/EBPα-regulated products in that process suggested that CDDP-1 may be regulated in the course of neutrophilic differentiation of various immature myeloid cell lines. CDDP-1 mRNA expression was examined in 32D clone 3 myoblasts, MPRO promyelocytes, and bipotential HL-60 late myeloblasts that had been induced to differentiate. In all three cell lines, CDDP-1 mRNA was induced by 24 hours. As shown in FIG. 9, G-CSF induced differentiation of 32D clone 3 cells resulted in CDDP-1 mRNA reaching peak levels of mRNA expression ahead of myeloperoxidase mRNA expression, but was then down regulated while myeloperoxidase mRNA expression remained robust. In this experiment, cell viability could not be maintained past 5 days and thus, the temporal relationship of CDDP-1 mRNA expression to lactoferrin mRNA expression could not be examined.

In MPRO cells induced to differentiate using all-trans-retinoic acid (ATRA), peak CDDP-1 mRNA expression was coincident with lactoferrin mRNA expression, which appeared to be later than its expression in the 32D clone 3 cells. However, CDDP-1 mRNA expression initially showed a decrement in mRNA levels followed later by induction of expression with ATRA. The results are shown in FIG. 10. The results further showed that myeloperoxidase mRNA levels decreased with CDDP-1 mRNA levels suggesting that the expression of CDDP-1 mRNA was biphasic: a first period of elevated CDDP-1 mRNA expression associated with the transcription of primary granule protein-encoding genes (myeloperoxidase) and a second period of elevated CDDP-1 mRNA expression associated with transcription of secondary granule protein-encoding genes (lactoferrin).

In HL-60 cells, myeloperoxidase mRNA expression was relatively high in uninduced cells and lactoferrin mRNA expression was not observed (data not shown), making it difficult to place CDDP-1 mRNA expression in a temporal sequence with these markers of neutrophilic differentiation. However, CDDP-1 mRNA expression induction parallels that of C/EBPε in these cells, placing its expression after acquisition of C/EBPα mRNA expression, but prior to peak expression of C/EBPβ and E/EBPδ. In contrast to the induction of CDDP-1 mRNA with neutrophilic differentiation in the three cell lines examined, CDDP-1 mRNA was downregulated with monocytic differentiation of HL-60 cells (FIG. 11). This is consistent with the lack of CDDP-1 mRNA expression in mature macrophage cell lines that was observed in FIG. 6. Thus, CDDP-1 mRNA expression is associated with neutrophilic as opposed to monocytic differentiation. The data collectively suggest a role in the later stages of neutrophilic differentiation, being similar to that of C/EBPε (MPRO, FIG. 10; HL-60, FIG. 11). In relation to the expression of genes encoding granule proteins, the timing of CDDP-1 mRNA expression is biphasic: CDDP-1 mRNA expression is associated with induction of myeloperoxidase mRNA expression (32D clone 3, FIG. 9) and again with the later induction of lactoferrin mRNA expression (MPRO, FIG. 10). CDDP-1 mRNA expression is thus, first observed at the promyelocyte stage of differentiation.

In order to better explore earlier time points in the course of neutrophilic differentiation, expression of CDDP-1 mRNA during myeloid differentiation of EML-C1 cells (Tsai et al., Genes & Dev. 8: 2831–2841 (1994)), a hematopoietic stem cell line, was examined. The Northern analysis shown in FIG. 12 of RNA isolated over a time course of ATRA-induced differentiation showed CDDP-1 mRNA to be transiently expressed in parallel to myeloperoxidase mRNA expression. This is consistent with the data obtained from the differentiation of 32D clone 3 myeloblasts shown in FIG. 9. GM-CSF-treated products of EML-C1 differentiation are blocked at the promyelocyte stage unless further treated with retinoic acid (Tsai et al., ibid.). MPRO, which displayed induction of CDDP-1 mRNA at the point of lactoferrin induction (as shown in FIG. 10), is analogous to such promyelocytes (Tsai et al., ibid.; Tsai and Collins, Proc. Natl. Acad. Sci. USA 90: 7153–7157 (1993)) and its differentiation could be considered an extension of the EML-C1 time course. Thus, the results from EML-C1 are consistent with a biphasic induction of CDDP-1 mRNA occurring first with myeloperoxidase mRNA induction and then again with lactoferrin mRNA induction indicating that CDDP-1 has a role in both early and later stages of myeloid differentiation. An analysis of a more complete time course of 32D clone 3 differentiation and further differentiation of the products of retinoic acid-induced differentiation of EML-C1 with GM-CSF and retinoic acid should clearly demonstrate that CDDP-1 induction is biphasic.

Figure 14:
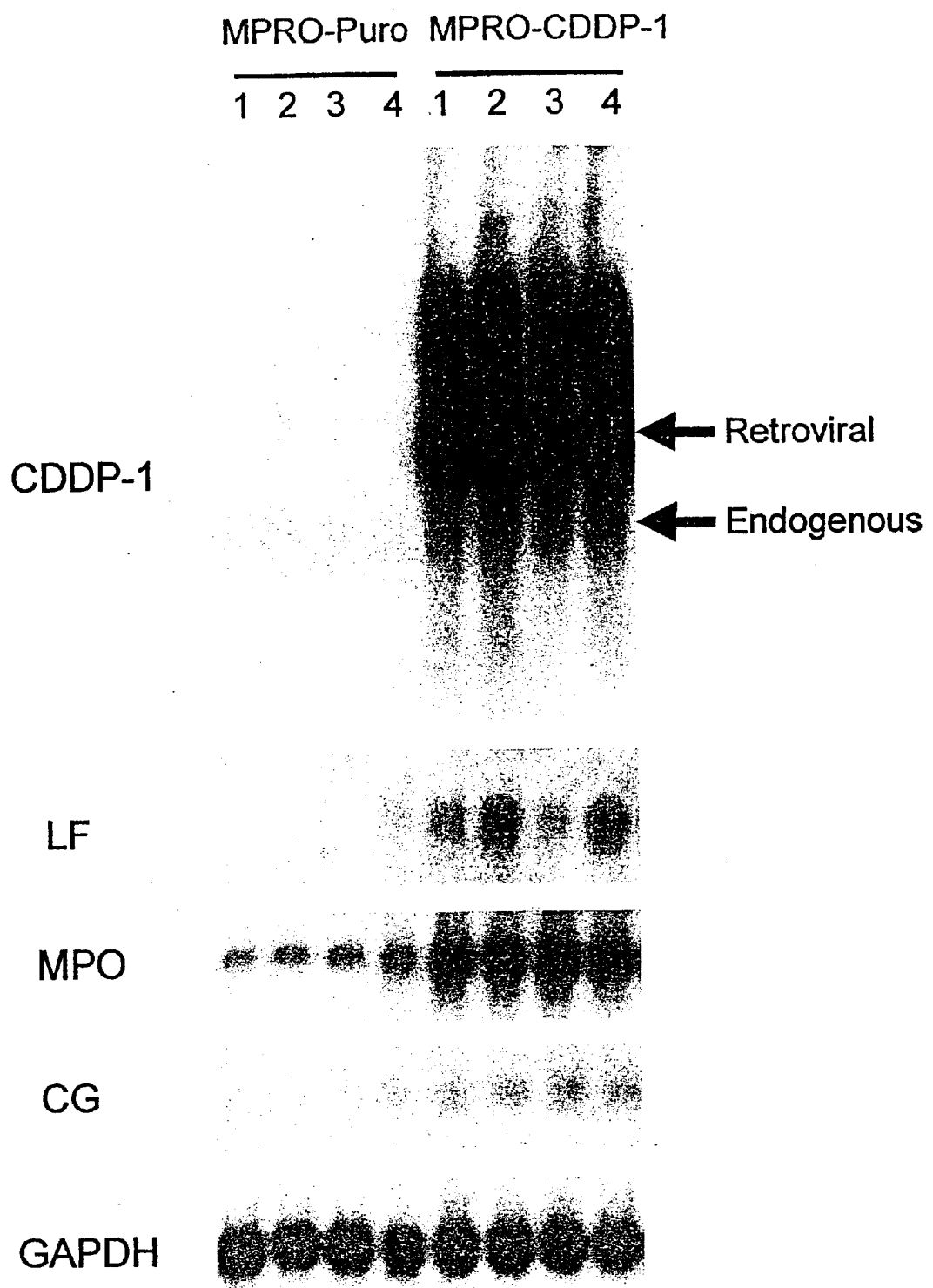
FIG. 14 shows a Northern blot of RNA isolated from 4 independent populations of MPRO cells infected with a control retrovirus (Puro) and 4 independent populations infected with a CDDP-1 expressing retrovirus (CDDP-1). The blot was successively hybridized with nucleic acid probes for CDDP-1, myeloperoxidase (MPO), lactoferrin (LF), cathepsin G (CG), and glyceraldehyde-3-phosphate dehydrogenase (GAPDH).
Figure 15:
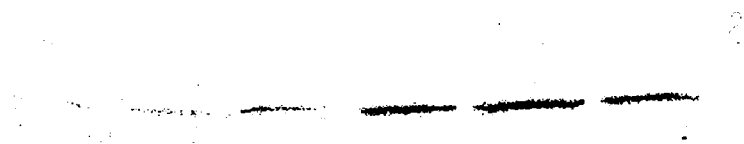
FIG. 15 shows a Western blot using CDDP-1-specific antibody showing elevated levels of CDDP-1 protein expression in three independent MPRO transductants of CDDP-1 (MPRO-CDDP-1) in comparison to control transductants (MPRO-Puro).

Constitutive Overexpression of CDDP-1 in MPRO Promyelocytes Promotes Their Differentiation. The close temporal association of CDDP-1 mRNA with mRNA from genes encoding granule proteins suggested that CDDP-1 encoded a novel granule protein or a novel regulator of granule protein expression. In order to determine the function of the protein encoded by the CDDP-1 mRNA, stable transductants were produced of MPRO cells using either a retroviral vector constitutively expressing CDDP-1 mRNA or an "empty vector" control. The vector used was pBABE-Puro, which allowed selection of stably transduced cells by puromycin selection (Morgenstern and Land, Nuc. Acids Res. 18: 3587–3596 (1990)). Three independent retroviral transduction experiments were carried out, generating a total of 10 cell populations overexpressing CDDP-1 mRNA, as well as twelve control populations. RNA was isolated from all of these cell populations and analyzed by Northern blot. As shown in FIG. 13, all of these CDDP-1 transductants expressed high levels of vector-derived CDDP-1 mRNA. Significantly, six of the populations transduced with the vector showed a more differentiated neutrophilic phenotype than the control populations. They showed a higher proportion of band form and polymorphonuclear cells (FIG. 13) and elevated levels of mRNAs encoding the primary granule proteins, myeloperoxidase, cathepsin G, and lysozyme. Four of the CDDP-1 transductants also showed elevated levels of lactoferrin mRNA (FIG. 14). Lactoferrin is a secondary granule protein that is only expressed after the more mature myelocyte stage of neutrophilic differentiation. A Western blot confirmed that CDDP-1 transductants also expressed elevated levels of CDDP-1 protein in comparison to control transductants (FIG. 15). Thus, CDDP-1 appeared to play a role in regulating the expression of granule protein RNAs. Furthermore, when the neutrophilic CDDP-1 transductants were treated with ATRA to induce differentiation, they all displayed a more rapid morphological differentiation than control populations with band cells and polymorphonuclear cells consistently appearing a day ahead of controls (FIG. 16).

Figure 17:
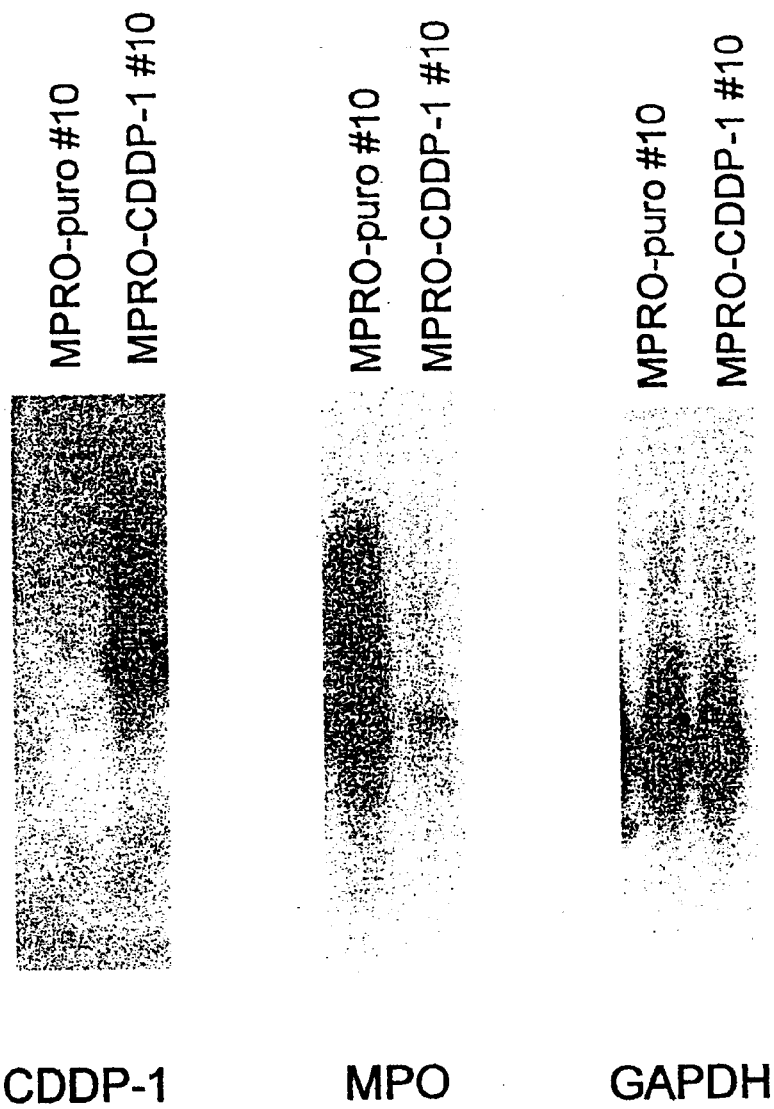
FIG. 17 shows a Northern blot of RNA isolated from a population of MPRO cells infected with a control retrovirus (Puro #10) and a population of MPRO infected with CDDP-1 expressing retrovirus (CDDP-1 #10). The blot was successively hybridized with probes for CDDP-1, myeloperoxidase (MPO), and glyceraldehyde-3-phosphate dehydrogenase (GAPDH).

Of particular interest were two of the CDDP-1 transductants, which showed morphological features suggesting monocyte/macrophage differentiation. These transductants had become very adherent to their culture plates with typical monocytic morphology: higher cytoplasm/nucleus ratio, pseudopods, and a foamy cytoplasm with many vesicles (FIG. 13). A Northern blot analysis of these cells showed diminished levels of myeloperoxidase mRNA expression compared to controls (FIG. 17). This is consistent with having undergone monocytic differentiation. Two of the CDDP-1 mRNA overexpressing populations showed no dramatic differences from the control populations. In light of these results, these data suggest that CDDP-1 has a role in promoting both the neutrophilic and monocytic differentiation of MPRO promyelocytes.

CDDP-1 was upregulated upon ATRA-induced differentiation of HL60, MPRO, and EML-C1 cell lines (FIGS. 10, 11, and 12). When CDDP-1 was overexpressed in MPRO cells, CDDP-1 facilitated ATRA-induced neutrophil differentiation (FIG. 16). In addition, a weak homology (31% identity over a 101 amino acid region) was found between CDDP-1 and Silencing Mediator of Retinoid and Thyroid hormone action (SMRT), a transcriptional co-repressor protein for retinoic acid receptor (NCBI). These results suggested that CDDP-1 may be an effector protein in retinoic acid signaling. However, transient transfection assays in CV-1 cells of CDDP-1 using a retinoic acid response element (RARE) promoter-reporter showed no consistent activation of the reporter by CDDP-1 either in the presence or absence of retinoic acid receptor $\alpha$ and retinoid-X receptor $\alpha$ expression, or in the presence or absence of ATRA (data not shown).

To further explore the mechanism of CDDP-1 in promoting myelomonocytic differentiation, a series of transient transfection experiments were performed in P388T lymphoblastic cells using promoter-reporter constructs driven by several promoters that are active in myeloid cells including those for myeloperoxidase, G-CSF receptor, M-CSF receptor, and IL-6 genes. However, CDDP-1 could not directly activate any of these promoter-reporter constructs (data not shown). Therefore, even though myeloperoxidase was upregulated in several instances of CDDP-1 overexpression in MPRO cells, that induction was not the result of direct activation. Rather, it is more likely that myeloperoxidase was upregulated as part of a more general differentiation program that was induced by CDDP-1 expression. The failure of CDDP-1 to activate the promoters for myeloperoxidase, G-CSF receptor, M-CSF receptor, and IL-6 demonstrated that CDDP-1 is likely not a direct activator of myeloid gene expression.

CDDP-1 Expression is Also Modulated in Erythroid and Mast Cell Differentiation. The Northern analysis of a panel of hematopoietic cells (FIG. 6) also showed that CDDP-1 mRNA was expressed in a broad range of hematopoietic cells, its expression being absent only in mature macrophage cell lines and a CD8+ T cell line. Since the EML-C1 cell line could be easily induced toward erythroid or mast cell differentiation, the pattern of CDDP-1 mRNA expression was examined over a time course for both differentiation pathways.

Figure 18:
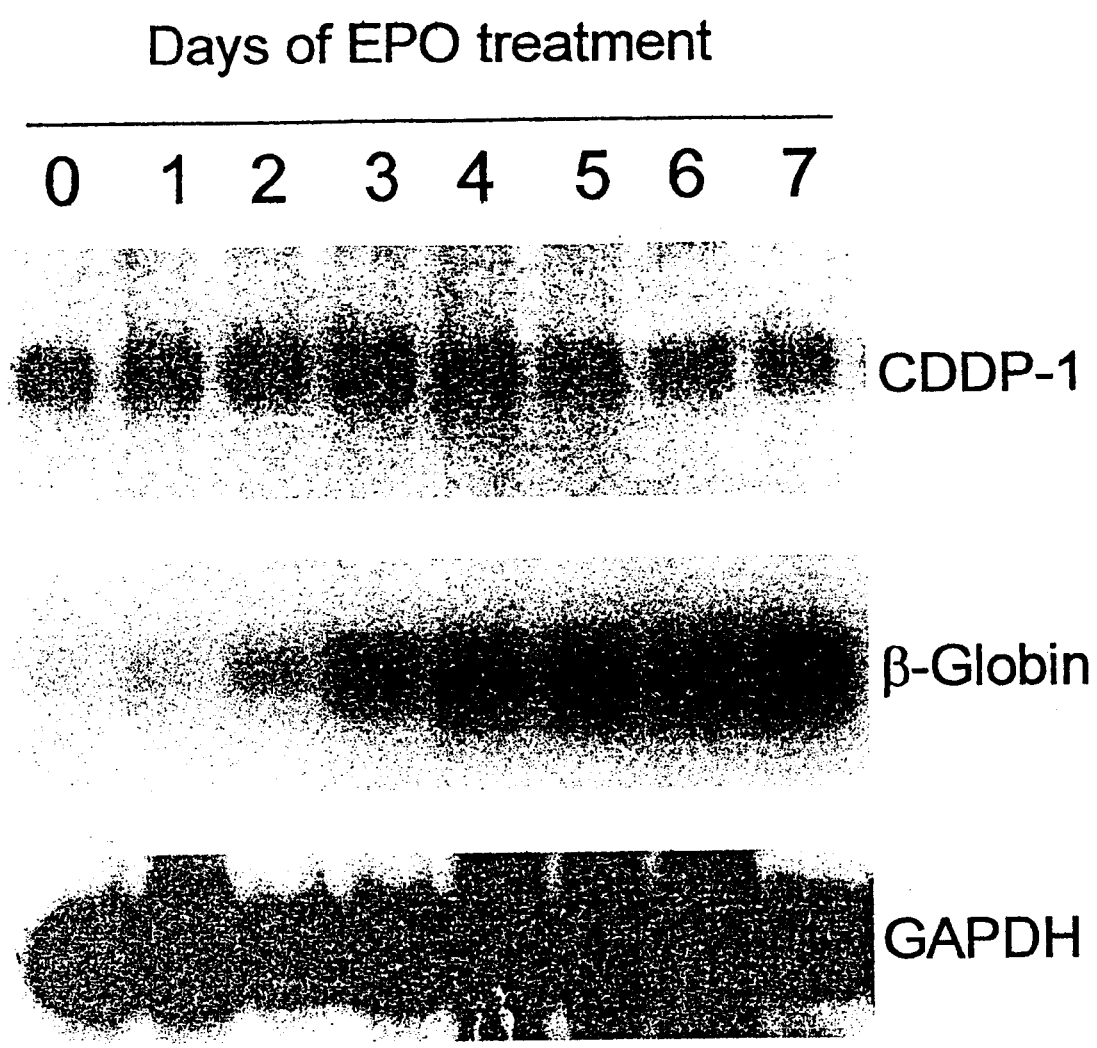
FIG. 18 shows a Northern blot of RNA isolated from a time course of EPO-induced differentiation of EML-C1 cells. The blot was successively hybridized with nucleic acid probes for CDDP-1, β-globin, and glyceraldehyde-3-phosphate dehydrogenase (GAPDH).

A Northern analysis of RNA isolated over a time course of erythropoietin (EPO)-induced differentiation of EMCL-C1 cells along the erythroid pathway showed CDDP-1 mRNA to be upregulated prior to $\beta$-globin mRNA expression, after the first day treatment in EPO. The highest level of CDDP-1 mRNA expression occurred on the third day of EPO treatment. Then, CDDP-1 mRNA was downregulated to basal levels as β-globin mRNA expression continued to increase until the seventh day of EPO treatment (FIG. 18). The Northern analysis in FIG. 6 had shown that CDDP-1 mRNA was induced upon DMSO-induced differentiation of the BB88 pre-erythroid cell line. A more complete time course, shown in FIG. 19, revealed the CDDP-1 mRNA to be induced by 10 hours post-induction, prior to induction of β-globin mRNA.

Northern analysis of RNA isolated over the time course of EML-C1 cells induced to differentiate along the mast cell pathway showed CDDP-1 mRNA to be upregulated after the first day of induction in WEHI-3 conditioned media (as a source for IL-3). High levels of CDDP-1 mRNA expression were maintained until the sixth day of treatment (FIG. 20). Thus, CDDP-1 is also regulated during the course of both erythroid and mast cell differentiation and may have a role in these processes.

Figure 21:
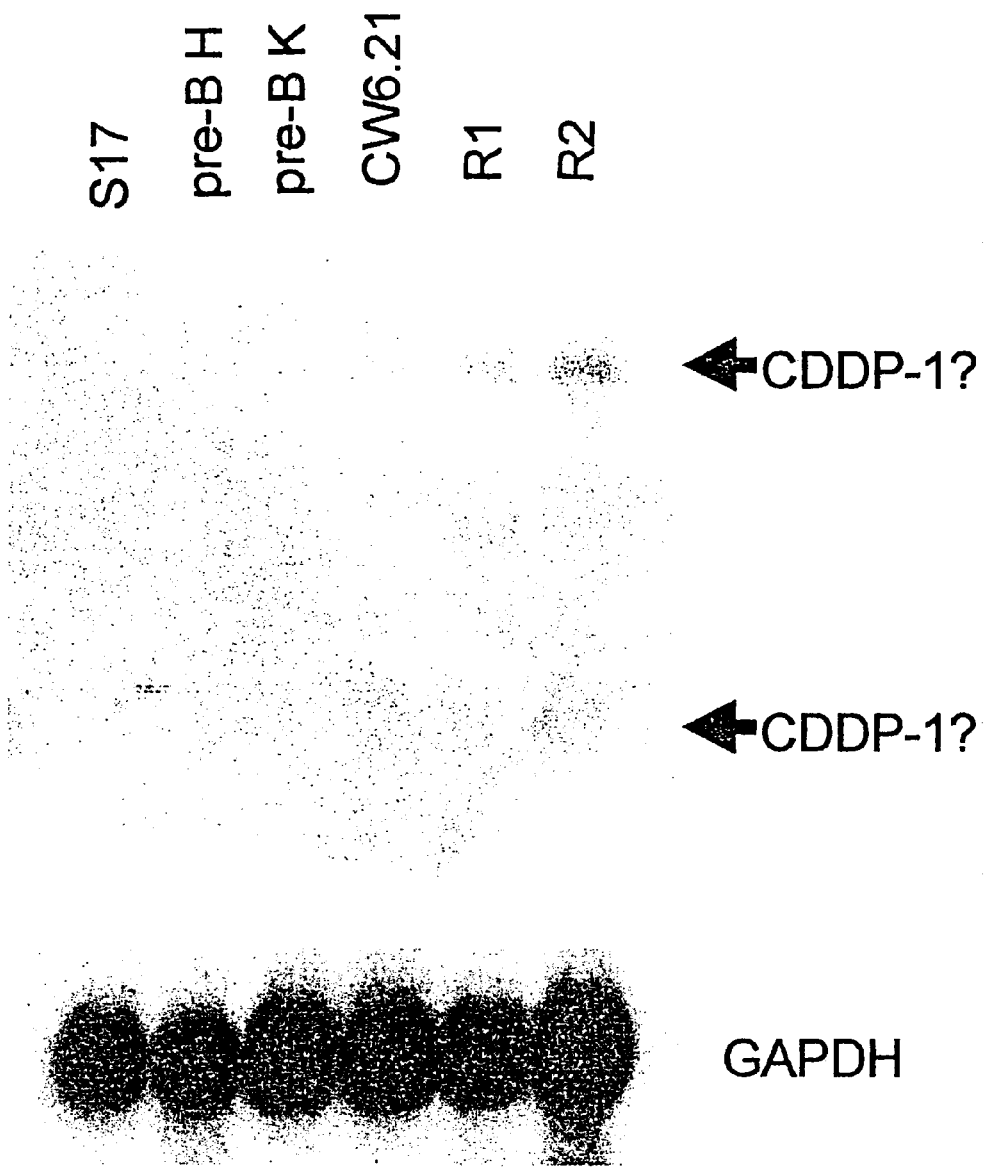
FIG. 21 shows a Northern blot showing two mRNA species detected in v-H-ras-transformed pre-B cell lines (R1 and R2) using a CDDP-1 nucleic acid probe. Non-transformed control pre-B cell lines (pre-BH and pre-BK) do not express CDDP-1 mRNA. S17 and CW6.21 are stromal cell lines which were used to culture the pre-B cells.

The EML-C1 cell line does not yield adequate numbers of lymphoid cells for Northern analysis. In order to examine differential expression of CDDP-1 during the course of B cell differentiation, RNAs were isolated from a panel of B cell lines representing several stages of B cell differentiation. Cell line 70Z is a pre-B cell line that is positive for cytoplasmic IgM but negative for cell surface IgM, cell line M12 is a B cell line that is negative for cell surface IgM, and cell lines R1 and R2 are pre-B cell lines transformed with v-H-ras (Schwartz et al., Mol. Cell. Biol. 6: 3221–3231 (1986)) that are negative for IgM and heavy chain. A Northern analysis (FIG. 6) showed that while CDDP-1 mRNA was expressed in pre-B (70Z) as well in B-cells (M12), there may be differential expression with regard to neoplastic transformation as shown by the Northern in FIG. 21. R1 and R2 expressed a higher molecular weight form of CDDP-1 mRNA (FIG. 21) than was observed in the various myeloid cell lines, the M12 B cell line, and the 70Z/3 pre-B cell line (see FIG. 6). On the other hand, FIG. 21 shows that non-transformed clone 1 and clone 3 pre-B cell lines (Whitlock et al., Cell 32: 903–911 (1983)) did not express CDDP-1 mRNA.

EXAMPLE 2

The analysis of the physiological significance of the CDDP-1 gene is analyzed through the construction of transgenic mice that contain "knockout" mutations in their endogenous chromosomal CDDP-1 alleles.

A murine genomic DNA library is screened for a clone that contains the murine CDDP-1 gene and flanking 5' and 3' DNA sequences based upon identity to the human CDDP-1 sequences of SEQ ID Nos. 1 and 3. The identified clone is subcloned into a plasmid vector such as pBluescript (Stratagene, La Jolla, Calif.) vectors. A targeting vector is constructed that contains the Herpes simplex thymidine kinase gene, the 5' flanking genomic fragment 5' to the CDDP-1 gene, the selectable neomycin resistance (NptII) determinant linked to a PGK promoter, and the 3' genomic fragment 3' of the CDDP-1 gene. The resulting targeting vector has the entire CDDP-1 gene replaced by the neomycin resistance determinant. Thus, recombination between the replacement vector and the chromosomal CDDP-1 gene effects deletion of the chromosomal CDDP-1 gene.

The vector is linearized at a unique restriction enzyme site outside the regions of homology and introduced into murine AB2.1 embryonic stem cells by electroporation. The electroporated cells are subjected to selection for G418 resistance and to selectivity to gancyclovar. Surviving clones are screened by Southern analysis for evidence of a targeted recombination event using probes that detect the vector and probes that detect the endogenous CDDP-1 gene. Positive clones that are identified are expanded in culture. Cells from the expanded clones are microinjected into developing blastocysts, which are then implanted into a foster mother and allow to develop to term.

Chimeric animals that are obtained are subsequently mated to produce both heterozygous and homozygous CDDP-1 deficient "knockout" mice.

EXAMPLE 3

To perform a nucleic acid-based assay for identifying chemical agents that cause myeloid differentiation by upregulating expression of CDDP-1, a series of cell cultures are prepared comprising EML-C1, 32D clone 3, BB88, HL-60, or MPRO cells as described in Example 1. The cell cultures are treated with the agent and at various time points thereafter, the cells are harvested and RNA isolated from the cells. The RNAs are resolved by denaturing gel electrophoresis, and transferred to membranes for Northern blotting as described in Example 1. In general cells are harvested at time 0 and 2, 4, 8, 24, 48, 72, 96, 120, and 144 hours after treatment.

In the case of 32D clone 3 cells and EML-C1 cells, the Northern blots are successively hybridized with labeled probes to CDDP-1 and myeloperoxidase (MPO), and a labeled probe to glyceraldehyde-3-phosphate dehydrogenase (GAPDH) as a positive control. Positive hybridization of the CDDP-1 and MPO probes after time 0 indicates that the agent effects myeloid differentiation.

In the case of MPRO cells, the Northern blots are successively hybridized with labeled probes to CDDP-1, MPO, and lactoferrin (LF), and a labeled probe to GAPDH. Positive hybridization of the CDDP-1 and the LF probe at around 48 hours post-treatment and loss of MPO hybridization around 48 hours post-treatment indicates that the agent effects myeloid differentiation.

In the case of BB88 cells and HL-60 cells, the Northern blots are successively hybridized with labeled probes to mRNA encoding CDDP-1 and β-globin, and a labeled probe to GAPDH. An increase in CDDP-1 mRNA expression after time 0 and expression of β-globin mRNA at around 72 hours post-treatment indicate that the agent effects myeloid differentiation.

As an alternative to Northern blots, the RNA encoding CDDP-1 can be detected and quantified by RT-PCR using methods well known in the art for designing PCR primers and performing PCR reactions.

EXAMPLE 4

To perform an immunologically-based assay for identifying chemical agents that cause myeloid differentiation by upregulating expression of CDDP-1, a series of cell cultures are prepared comprising EML-C1, 32D clone 3, BB88, HL-60, or MPRO cells as described in Example 1. The cell cultures are treated with the agent and at various time points thereafter, the cells are harvested and protein isolated from the cells. The proteins in the extracts are resolved by SDS-polyacrylamide gel electrophoresis, and transferred to membranes for Western blotting as described in Example 1. In general cells are harvested at time 0 and 2, 4, 8, 24, 48, 72, 96, 120, and 144 hours after treatment. An increase in expression of the CDDP-1 polypeptide indicates that the chemical agent effects cell differentiation.

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

We claim:

1. An isolated cDNA molecule that encodes a human C/EBP Differential Display Product-1 (CDDP-1), wherein the CDDP-1 consists essentially of the amino acid sequence set forth in SEQ ID NO:2.

2. An isolated cDNA molecule that encodes human C/EBP Differential Display Product-1 (CDDP-1), wherein the CDDP-1 consists essentially of the amino acid sequence set forth in SEQ ID NO:2 and the CDDP-1 promotes differentiation of murine promyelocytes (MPRO cells) along a neutrophilic, monocytic, or macrophage differentiation pathway.

3. The cDNA molecule of claim 1 or 2, wherein the cDNA molecule consists essentially of a nucleic acid sequence set forth in SEQ ID NO:1.

4. The DNA molecule of claim 3, wherein the cDNA molecule is detectably labeled.

5. An isolated human cDNA encoding CDDP-1 which consists essentially of the nucleotide sequence set forth in SEQ ID NO:1.

6. A vector comprising a nucleic acid molecule that encodes human C/EBP Differential Display Product-1 (CDDP-1) operably linked to a heterologous promoter wherein the CDDP-1 consists essentially of the amino acid sequence set forth in SEQ ID NO:2 and the CDDP-1 promotes differentiation of murine promyelocytes (MPRO cells) along a neutrophilic, monocytic, or macrophage differentiation pathway.

7. A vector comprising a nucleic acid molecule that encodes human C/EBP Differential Display Product-1 (CDDP-1) which consists essentially of the amino acid sequence set forth in SEQ ID NO:2, and that is operably linked to a heterologous promoter.

8. The vector of claim 6 or 7, wherein the CDDP-1 is encoded by the DNA molecule consisting essentially of the nucleic acid sequence of SEQ ID NO:1.

9. The vector of claim 6 or 7, wherein the vector comprises a retrovirus or a plasmid.

10. A vector containing a nucleic acid consisting essentially of the nucleotide sequence set forth in SEQ ID NO:1 and wherein the DNA is operably linked to a heterologous promoter.

11. A cell line harboring a vector containing a nucleic acid consisting essentially of the nucleotide sequences set forth in SEQ ID NO:1 and wherein the nucleic acid is operably linked to a heterologous promoter.

* * * * *